United States Patent
Ludwig

(10) Patent No.: US 9,646,133 B2
(45) Date of Patent: May 9, 2017

(54) COMPUTER SYSTEM AND MICROFLUIDIC INSTRUMENTATION FOR NEXT-GENERATION BIOLOGICAL SIGNALING NETWORK RESEARCH AND APPLICATIONS

(75) Inventor: Lester F. Ludwig, San Antonio, TX (US)

(73) Assignee: Lester F. Ludwig, San Antonio, TX (US)

( * ) Notice: Subject to any disclaimer, the term of this patent is extended or adjusted under 35 U.S.C. 154(b) by 1494 days.

(21) Appl. No.: 13/157,304

(22) Filed: Jun. 9, 2011

(65) Prior Publication Data

US 2011/0307182 A1 Dec. 15, 2011

Related U.S. Application Data

(60) Provisional application No. 61/353,194, filed on Jun. 9, 2010.

(51) Int. Cl.
*G06F 19/12* (2011.01)
*G06F 19/18* (2011.01)
(Continued)

(52) U.S. Cl.
CPC ......... *G06F 19/18* (2013.01); *G01N 35/1095* (2013.01); *A61B 5/14503* (2013.01); *G06F 19/12* (2013.01); *G06F 19/24* (2013.01)

(58) Field of Classification Search
CPC .......... G06F 19/12; G06F 19/24; G06F 19/18; G01N 35/1095; A61B 5/14503
(Continued)

(56) References Cited

U.S. PATENT DOCUMENTS 6,384,905 B1 * 5/2002 Barrows .................. 356/28
6,623,860 B2 * 9/2003 Hu et al. .................. 428/411.1
(Continued)

OTHER PUBLICATIONS

Microengineered Platforms for Cell MechanobiologyAnnual Review of Biomedical Engineeringvol. 11: 203-233 (Volume publication date Aug. 2009: First published online as a Review in Advance on Apr. 13, 2009).*

*Primary Examiner* — Shogo Sasaki
(74) *Attorney, Agent, or Firm* — Procopio, Cory, Hargreaves & Savitch LLP

(57) ABSTRACT

A computer-controlled micro-instrumentation biochemical reaction environment system includes an electrically-controllable microfludic routing system, at least one microreaction chamber, at least one micro-instrumentation device, and at least one electronic microprocessor. The microreaction chamber supports at least one chemical reaction associated with a biological signaling pathway. The micro-instrumentation device measures at least one physical quantity associated with the signaling pathway. The microprocessor transmits electrical control signals, receives electrical measurement signals, and executes at least one software algorithm. The microreaction chamber is connected to the microfludic routing system to receive and transmit at least a fluid or gas, and the electronic microprocessor receives electrical measurement signals from the micro-instrumentation device via a first electric interface and transmits electrical control signals to electrically-controllable microfludic routing system via a second electrical interface.

20 Claims, 19 Drawing Sheets

(51) Int. Cl.
*G01N 35/10* (2006.01)
*G06F 19/24* (2011.01)
*A61B 5/145* (2006.01)

(58) Field of Classification Search
USPC .......................................................... 422/501
See application file for complete search history.

(56) References Cited

U.S. PATENT DOCUMENTS

2002/0012616 A1* 1/2002 Zhou et al. .................... 422/130
2004/0223874 A1* 11/2004 Numajiri ......................... 422/58
2005/0204829 A1* 9/2005 Cohen ......................... 73/861.53

* cited by examiner

COMPUTER SYSTEM AND MICROFLUIDIC INSTRUMENTATION FOR NEXT-GENERATION BIOLOGICAL SIGNALING NETWORK RESEARCH AND APPLICATIONS

CROSS-REFERENCE TO RELATED APPLICATIONS

Pursuant to 35 U.S.C. §119(e), this application claims benefit of priority from Provisional U.S. Patent application Ser. No. 61/353,194, filed Jun. 9, 2010, the contents of which are incorporated by reference.

COPYRIGHT & TRADEMARK NOTICES

A portion of the disclosure of this patent document may contain material, which is subject to copyright protection. Certain marks referenced herein may be common law or registered trademarks of the applicant, the assignee or third parties affiliated or unaffiliated with the applicant or the assignee. Use of these marks is for providing an enabling disclosure by way of example and shall not be construed to exclusively limit the scope of the disclosed subject matter to material associated with such marks.

BACKGROUND OF THE INVENTION

The invention is directed to innovative tools in proteomics, metabolomics, kinomics, and bioinformatics. The invention is also directed to the use of microfluidic/nanoliter biochemical signaling pathway devices as analysis/-synthesis/regulatory "biochemical chips" for implant in humans to control disease or pathologies and/or to provide therapies.

Implicit in these are individual sequences of chemical reactions, each of which begins with a chemical reaction of one kind, which, as it progresses or completes, subsequently initiates one or more chemical reactions of another kind. The latter reaction in turn causes one or more additional types of subsequent reactions to occur, and so on, to form chain that can act as a chemical channel for carrying information. Typically the products produced in a given chemical reaction are such that they initiate or inhibit one or more reactions that follow it. Because the information is carried by a stimulus being transformed by each reaction in the chain, the term "transduction" has been applied, in analogy with transducers that transform an input optical, mechanical, electrical, or mechanical stimulus into an output stimulus of another type. The structured interactions form a network, hence the terms signaling network and signal transduction network.

SUMMARY OF THE INVENTION

Features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

In an embodiment, the invention comprises a computer-controlled micro-instrumentation biochemical reaction environment system which in turn comprises:

an electrically-controllable microfludic routing system for the controlled transport of picoliter to nanoliter quantities of fluids and gases, the microfludic routing system comprising at least a first electrical interface for receiving electrical signals used for control of the routing of fluids and gases provided by the microfludic routing system;

at least one microreaction chamber for supporting at least one chemical reaction associated with a biological signaling pathway;

at least one micro-instrumentation device for measuring at least one physical quantity associated with the signaling pathway, the micro-instrumentation device producing at least one electrical measurement signal, the micro-instrumentation device further comprising a second electrical interface for transmitting the at least one electrical measurement signal; and at least one electronic microprocessor configured to transmit electrical control signals, to receive electrical measurement signals, and to execute at least one software algorithm;

wherein the microreaction chamber is connected to the microfludic routing system so as to receive at least one of a fluid or gas from the microfludic routing system and to transmit at least one of a fluid or gas to the microfludic routing system; and wherein the electronic microprocessor receives electrical measurement signals from at least the first electrical interface and further transmits electrical control signals to at least the second electrical interface.

In another aspect of the invention, the micro-instrumentation device is physically in contact with the contents of the microreaction chamber.

In another aspect of the invention, the micro-instrumentation device is physically in contact with the contents of a fluid or gas travelling through the microfludic routing system.

In another aspect of the invention, the electronic microprocessor is further electrically connected to an external signal interface.

In another aspect of the invention, the electronic microprocessor transmits electrical measurement signals to the external signal interface.

In another aspect of the invention, the electronic microprocessor receives electrical control signals from the external signal interface.

In another aspect of the invention, the algorithm executing on the electronic microprocessor processes information represented in the at least one electrical measurement signal so as to produce a processed measurement data.

In another aspect of the invention, the electronic microprocessor transmits processed measurement data to the external signal interface.

In another aspect of the invention, the algorithm executing on the electronic microprocessor comprises a control algorithm that produces control information used for control of the routing of fluids and gases provided by the microfludic routing system.

In another aspect of the invention, the micro-instrumentation device comprises at least one LED.

In another aspect of the invention, the electronic microprocessor generates LED control signals to control the LED comprised by the micro-instrumentation device.

In another aspect of the invention, the system is further configured for use with numerical signaling pathway model system.

In another aspect of the invention, the system is further configured for use in living organism as in living organisms for the monitoring of at least one signaling pathway.

In another aspect of the invention, the system is further configured for use in living organism as in living organisms for the monitoring of at least metabolic process.

In another aspect of the invention, the system is further configured for use in living organism for analysis of the operation of at least one signaling pathway.

In another aspect of the invention, the system is further configured for use in living organism as in living organisms for synthesis of a chemical agent for use in affecting at least one signaling pathway.

In another aspect of the invention, the system is further configured for use in living organism as in living organisms for regulation of at least one signaling pathway.

In another aspect of the invention, the system is further configured for use in living organism as in living organisms for regulation of at least one metabolic process.

In another aspect of the invention, the system is further configured for use in living organism to administer a chemical agent for use in affecting at least one signaling pathway.

In another aspect of the invention, the system is further configured for use in living organism to administer a therapy delivery for use in affecting at least one signaling pathway.

BRIEF DESCRIPTION OF THE DRAWINGS

The above and other aspects, features and advantages of the present invention will become more apparent upon consideration of the following description of preferred embodiments taken in conjunction with the accompanying drawing figures.

DETAILED DESCRIPTION OF THE PREFERRED EMBODIMENTS

In the following, numerous specific details are set forth to provide a thorough description of various embodiments. Certain embodiments may be practiced without these specific details or with some variations in detail. In some instances, certain features are described in less detail so as not to obscure other aspects. The level of detail associated with each of the elements or features should not be construed to qualify the novelty or importance of one feature over the others.

In the following description, reference is made to the accompanying drawing figures which form a part hereof, and which show by way of illustration specific embodiments of the invention. It is to be understood by those of ordinary skill in this technological field that other embodiments may be utilized, and structural, electrical, as well as procedural changes may be made without departing from the scope of the present invention.

Figure 1:
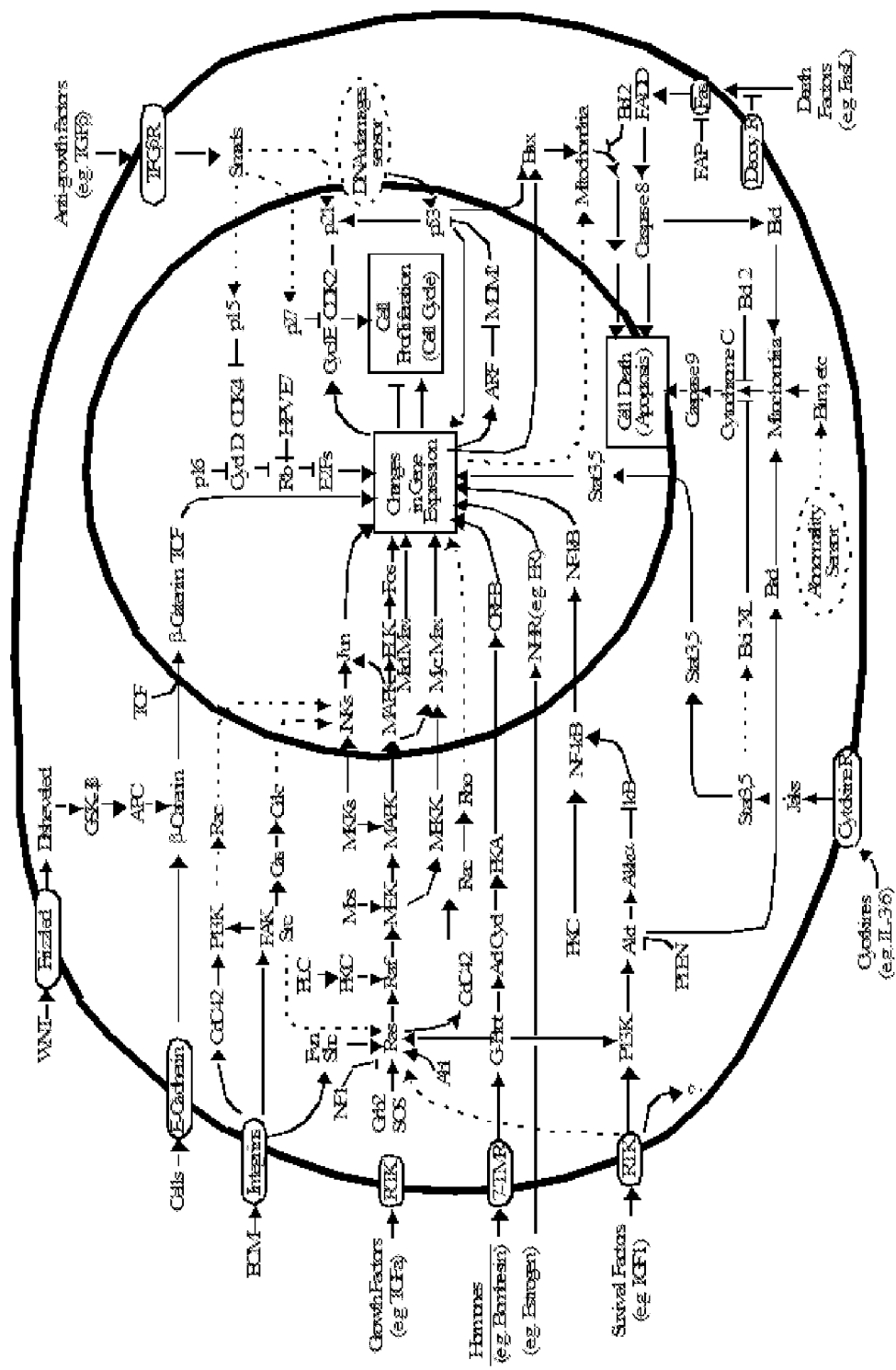
FIG. 1 (adapted from [27]) shows a simplified rendering of major pathways in an archetypical mammalian cell, omitting for example nearly all feedback loops, most calcium signaling [7], etc.

FIG. 1 (adapted from [27]) shows a simplified rendering of major pathways in an archetypical mammalian cell, but is hardly representative. Much is omitted, for example nearly all feedback loops, most calcium signaling [7], etc., the understanding of all of which is rapidly expanding. Nearly every pathway depicted in FIG. 1 has extensive additional structure, with new pathways, crosstalk, and enzyme properties discoveries reported monthly.

Figure 2:
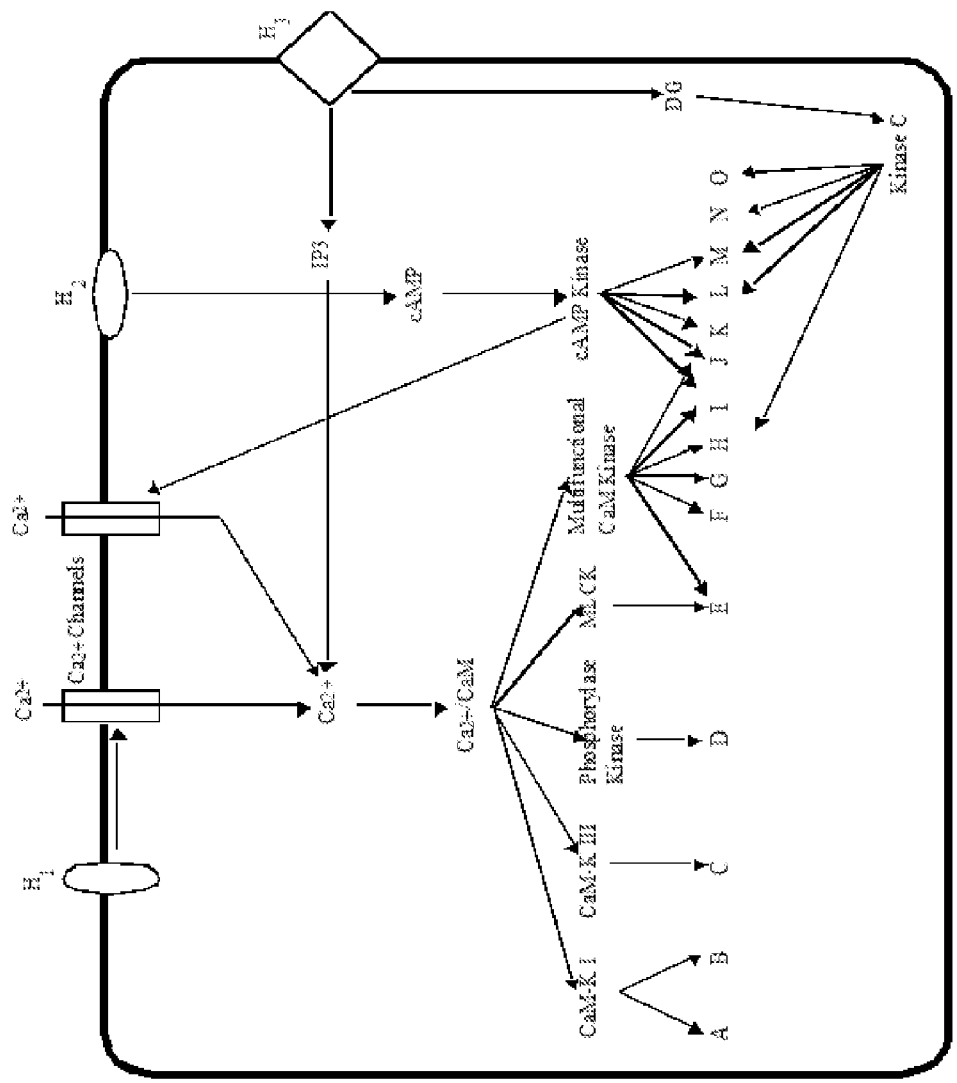
FIG. 2 (adapted from [32]) depicts a categorical pathway representation calling out specific enzymes and roles of calmodulin and cAMP (cyclic Adenosine MonoPhosphate), noting the extensive number of roles and associated pathways involving calmodulin, cAMP, and associated kinases (enzymes transferring phosphate groups).

As to intracellular calcium signaling omitted in FIG. 1, FIG. 2 (adapted from [32]) depicts a categorical pathway representation calling out specific enzymes and roles of calmodulin and cAMP (cyclic Adenosine MonoPhosphate), noting the extensive number of roles and associated pathways involving calmodulin, cAMP, and associated kinases (enzymes transferring phosphate groups).

Figure 3:
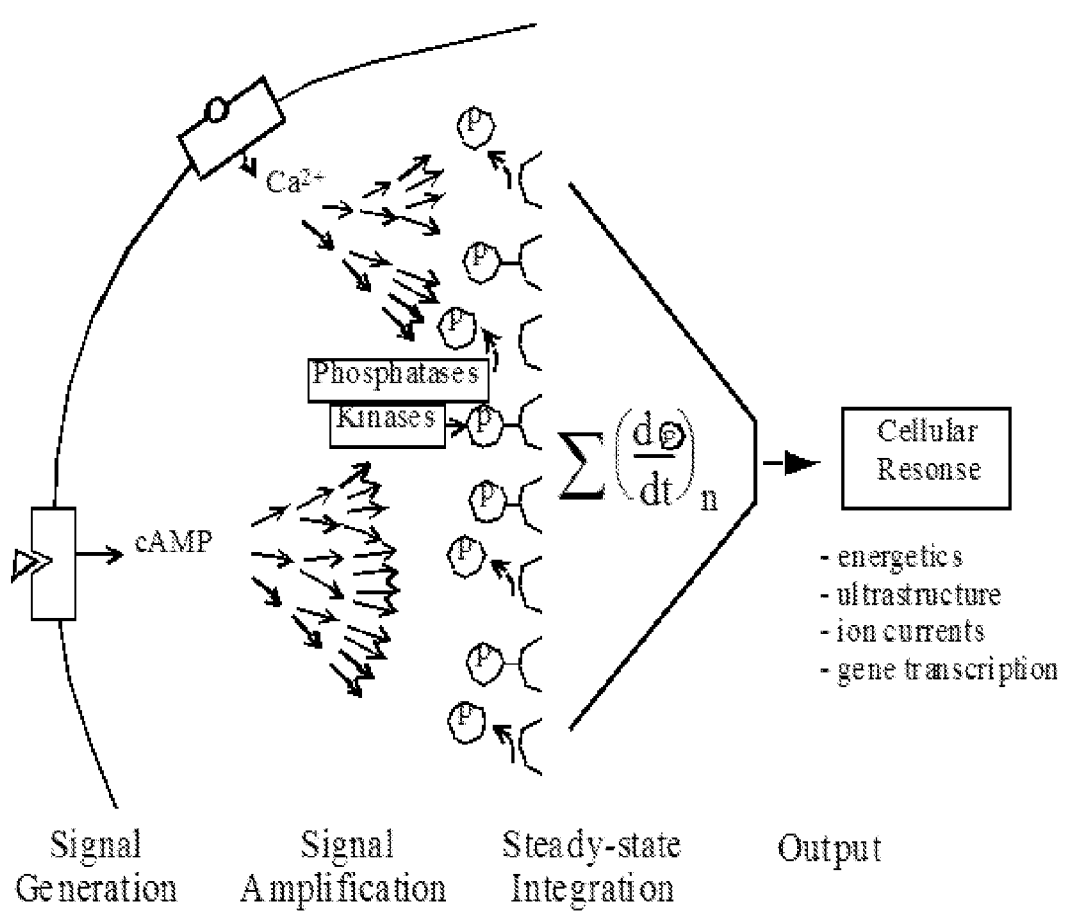
FIG. 3 (adapted from [17]) depicts roles of calcium and cAMP showcasing the categorical functions of signal generation, signal amplification [49,65], multiple-source signal integration, and outputs directing cellular response.

FIG. 3 (adapted from [17]) depicts roles of calcium and cAMP showcasing the categorical functions of signal generation, signal amplification, multiple-source signal integration, and outputs directing cellular response. Hormones, cytokines, growth factors, ion channels, ligands, and receptors, among others, provide a means for signaling among cells and regional or global metabolic control by other aspects and elements of an organism and/or the environment.

Figure 4:
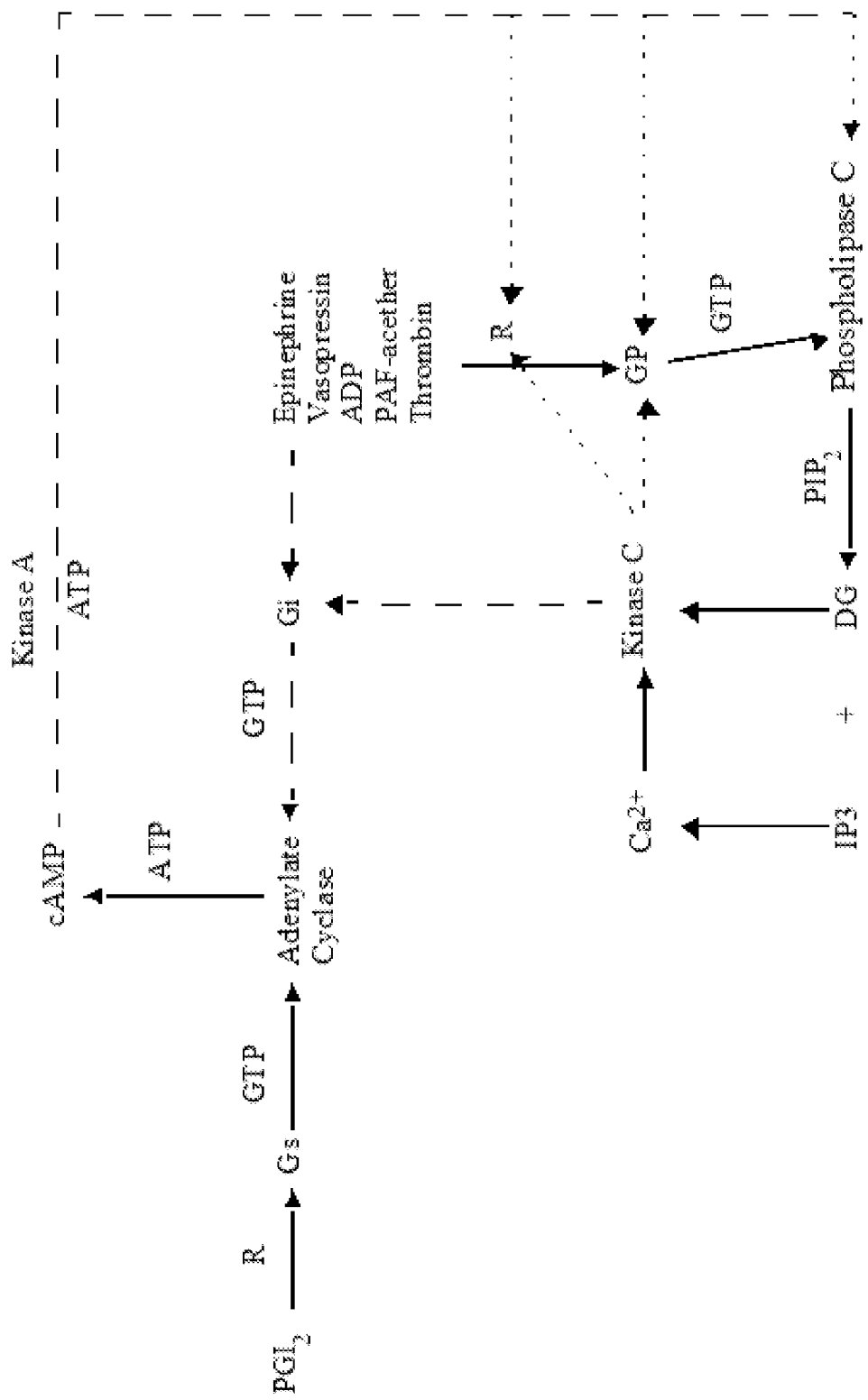
FIG. 4 (adapted from [14]) depicts one small aspect of intracellular calcium metabolism, and including exemplary feedback paths. In general, new feedback paths are being sporadically identified.

FIG. 4 (adapted from [14]) depicts one small aspect of intracellular calcium metabolism, and including exemplary feedback paths. In general, new feedback paths are being sporadically identified. For example, feedback recently found and added to models for Ras/RAF/MEK/ERK kinase signaling model which changes the understanding of the dynamics significantly [29].

In naturally occurring biological systems, there are astonishing numbers and wide-ranging types of signaling and signal transduction communications channels. A startling 20% of the coding genes in humans encode for proteins directly involved in signal transduction [36]. Although under study for year, the complexity of signaling networks is just beginning to be appreciated and somewhat cataloged. A large number of signaling transduction networks are known, albeit most in only early stages of identification, and these are typically barely understood in isolation and even less understood in their broader intertwined operations and roles within the organism [45,46]. Vast numbers of new findings and hypotheses publish monthly.

Roles of Signaling in Disease

The constituent biochemical signaling and signal transductions in the environments where they occur are extraordinarily dependable, implementing or supporting almost every life process on the planet. However, biochemical signal transductions can go awry. Such signal transduction process failure has been explicitly linked to disease, illness, and pathology, including cancer. The communication between the pathways of signal transduction such as TRK signaling, growth factors (VEGF, TGFs, IGF, EGF, PDGF, and FGF), NOTCH signaling, cAMP signaling, PI3K/PTEN/Akt, WNT signaling, RAS signaling, pRb tumor suppressor, Rel/NF-κB/IκB, STAT, steroid hormone receptor signaling, calcium signaling, and cell death signaling (death receptor and mitochondria pathway) plays rule in directly and indirectly to human disorders. For example, dysregulation of the Signal Transducer and Activator of Transcription ("Stat") proteins, RAF kinase signaling pathways (such as Ras/RAF/MEK/ERK), cell cycle Cyclin-CDK complexes aspects of mitosis-promoting factors, growth factor roles in chemical signaling pathways, and many other signaling pathways are implicated in cancer. Moreover, inappropriately triggered cell death programs critical involve neurodegenerative diseases, multiple sclerosis, Huntington's disease. A few of the many known or conjectured other examples of signaling pathways involved in disease are found in [1, 9, 10, 12, 15, 25, 30] and a host of articles publishing monthly worldwide. Variations in signaling give rise to disease, illness, and pathology, and in turn disease, illness, and pathology can give rise to variations in signaling. Variations in signaling can result from variations in the ambient reaction environment or from unintended "cross talk" [21, 31, 37] (coupling) between individual reactions in two or more biochemical signal transduction pathways (or even within the same pathway). In general modes of variation in signaling and resulting behavior remain largely a mystery. Characterization of signal transduction crucial regulation of cell communication and cross-talk is potential for understanding the pathology, human disorders, including the development of therapeutic innovations [37].

Analytical Models of Signaling Pathways and their Behavior

Over the last few decades there has been considerable increase in interest in analytical study of signaling and signal transduction networks within biological systems. Such study has yielded tremendous value in the understanding of disease, metabolism, drug discovery, gene expression, and a number of other areas. Future study appears to hold rich promise, as these basic frameworks of biochemical communication are involved in almost all aspects of life processes. Additionally, these biochemical communications channels—together with their implicit controlling and regulatory structures—could potentially be adapted into future nanotechnology systems, manufacturing, and other non-life-science applications. Despite extensive analytical study of signal transduction thus far, the area remains poorly understood. Much effort and impressive success has been made identifying specific sequences of reactions in specific pathways and the constituents of these. However, the structure of specific reaction types are less understood and few dynamic behaviors have been reduced to representative mathematical models. Additionally, few of the needed rate constants determining dynamic behavior in mathematical models, have been viably measured in ways relevant to their in situ occurrences.

Further, in the known relatively accurate mathematical models, the true dynamics quite often comprise nonlinear differential equations. Few researchers can work well with these, and so often these nonlinear differential equations are linearized (removing their nonlinear character) and/or studied in steady-state equilibrium (setting all time derivatives to zero), thereby missing both the intrinsic nonlinearities and intrinsic dynamics. In other fields of study involving nonlinear differential equations (such as electronic communications, mechanics, chemical engineering, and dynamic control systems), it is through the detailed study of the nonlinear dynamics behavior that essential aspects of instability, trajectory bifurcations, sensitivity to outside disturbances at various specific points in the structure, and other key aspects relative to questions of robustness and failure modes are revealed. It is in part to these, as well as other related problems, shortcoming, and applications, that the present invention is directed.

As one example, it is clear that many aspects of signaling pathway dynamics, in particular that of enzyme/kinase cascades, are naturally structured as "bilinear" (or "affine") differential equations as identified at a high level in 1975 by H. T. Banks, et al. [2]. These types of nonlinear differential equations comprise terms involving the cross-product between state variables and control variables. As [2] pointed out, these terms naturally capture essential aspects of enzyme cascades (as well as those of other catalytic chemical reaction network models, immunology models, and epidemiology models). Bilinear differential equations have unique dynamic behaviors and complexities that are completely missed by commonly used simplifications such as linearization, equilibrium point solution from setting time derivatives to zero, etc. Additionally, many aspects of bilinear differential equation dynamics are not readily summarized or characterized by classical nonlinear differential equation techniques. Further, many key properties of applicable bilinear differential equations stem from underlying Lie algebra structures [8, 11, 18] which the inventor's earlier [20] and subsequent work shows readily lend themselves to algorithmic computation in a computer modeling tool.

Figure 5:
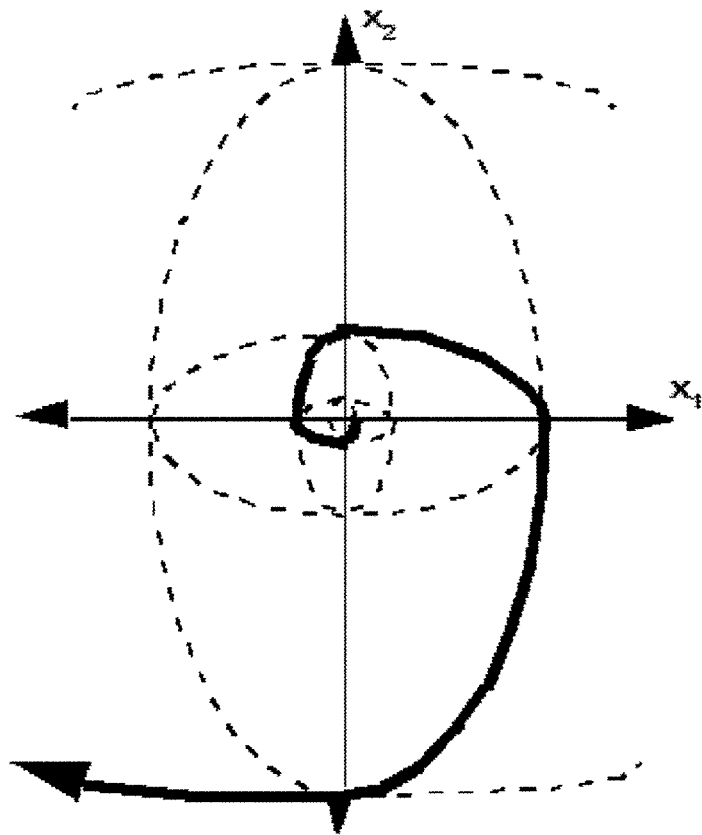
FIG. 5 shows an example where a stable elliptical trajectory with axis of eccentricity rotated by a small bounded periodic control variation can be "pumped" into unbounded instability [20].
Figure 6:
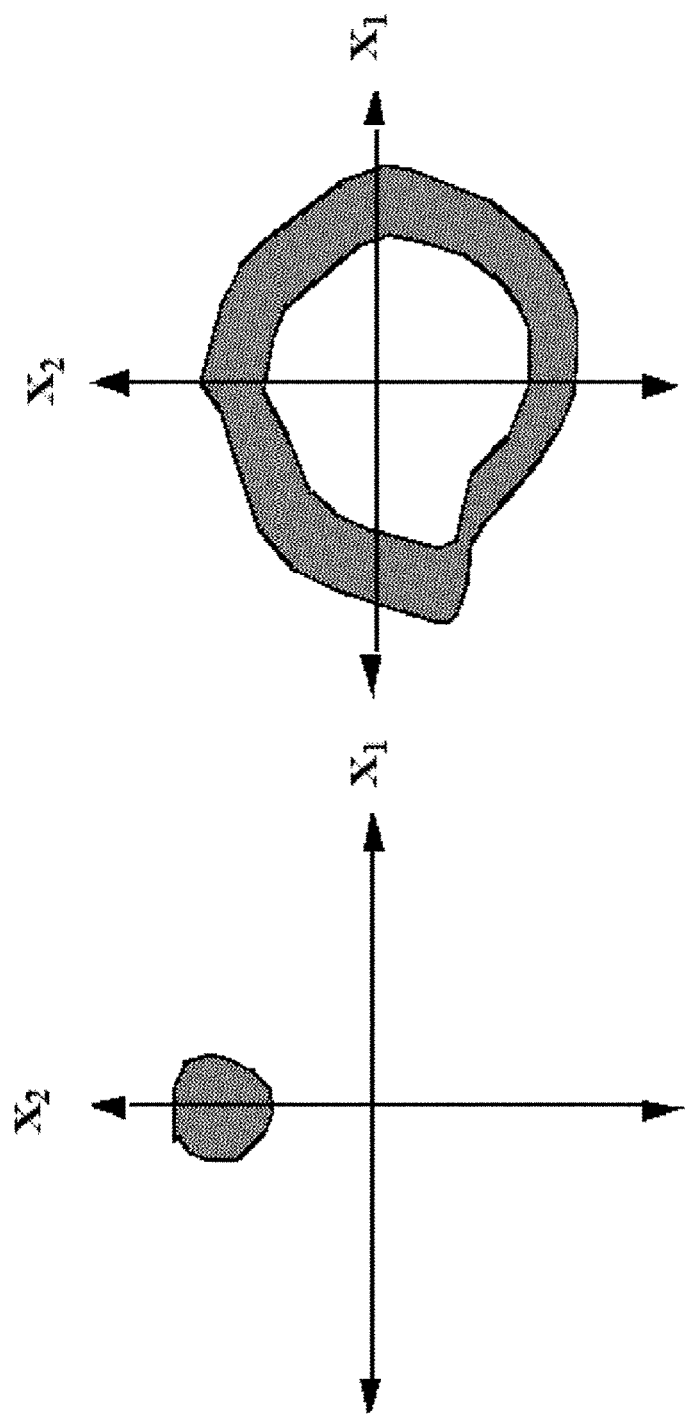
FIGS. 6A and 6B show an example of a reachable set of trajectory points that begins with a convex connected region but evolves to include a hole, thus defining forbidden states [11] and flow invariance violations [26].

In modeling linear dynamics, a separate "state" variable is used to represent the concentration of each relevant chemical species. Linear control systems relate rates of change in state variables to linear combinations of the state variables and externally adjusted control variables:

$$d\underline{x}/dt = A\underline{x} + B\underline{u}$$

where x is the vector of state variables, u is a vector of control variables, A and B are matrices [22]. In many signaling pathways, variations in concentration of one chemical species act as a "control" governing variations in concentration of another chemical species. In chemical systems involving enzymes or other catalytic processes, every newly available molecule of the first ("control") species catalytically acts to repeatedly create molecules of the second species. This multiplying operation among enzyme or catalytic concentrations mathematically amounts to one state variable multiplying another [2, 26], an operation naturally modeled by bilinear differential equations [24]. Specifically, bilinear control systems additionally relate the rates of change of state variables to cross-products of state variables with additional externally adjusted control variables:

$$d\underline{x}/dt = A\underline{x} + B\underline{u} + \sum_k [(\underline{u})_k N_k \underline{x}]$$

where (u)k denotes the kth component of the vector u. Control via linear state variable feedback, i.e., where control variables are linear combinations of state variables u=C x can introduce cross-products among pairs of state variables. Bilinear differential equations have many unusual behaviors and "hidden" instabilities. FIG. 5 shows an example where a stable elliptical trajectory with axis of eccentricity rotated by a small bounded periodic control variation can be "pumped" into unbounded instability [20]. FIGS. 6A and 6B show an example of a reachable set of trajectory points that begins with a convex connected region but evolves to include a hole, thus defining forbidden states [11] and flow invariance violations [26]. These and other behaviors are unlike anything found in linear differential equations, and there is no known comprehensive catalog of all possible behaviors of bilinear differential equations. Of noteworthy interest are Lie algebraic structures within bilinear dynamics that explicitly connect to stability and behavior of bilinear differential equations [8, 11, 18]. There is nothing like this in the behavior of linear differential equations. Thus linearizing enzyme cascade differential equations or only examining equilibrium conditions can completely miss key hidden stability issues.

Figure 7:
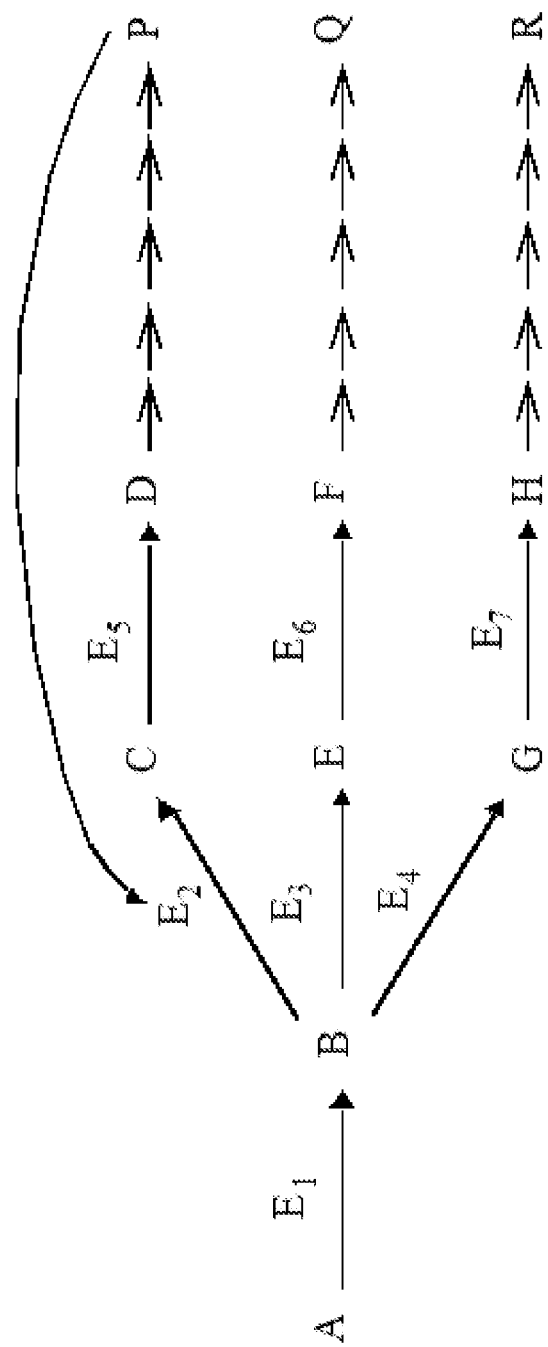
FIG. 7 (adapted from [35]) depicts an exemplary branched cascade arrangement, showing an exemplary feedback path closing one of the branches that can result from an individual state of an allosteric enzyme.

FIG. 7 (adapted from [35]) depicts an exemplary branched cascade arrangement, showing an exemplary feedback path closing one of the branches that can result from an individual state of an allosteric enzyme. This offers an initial hint at the types and degrees of complexity inherent in signaling pathways and signaling cascades, and specifically at the need for a computer tool so that these complex interactions among cascades can be studied. New feedback loops, new steps and elements of cascades, and new modulations of them are being discovered and reported every few days as research and understanding intensifies, yet to date even the surface of this area has barely been surveyed.

Figure 8:
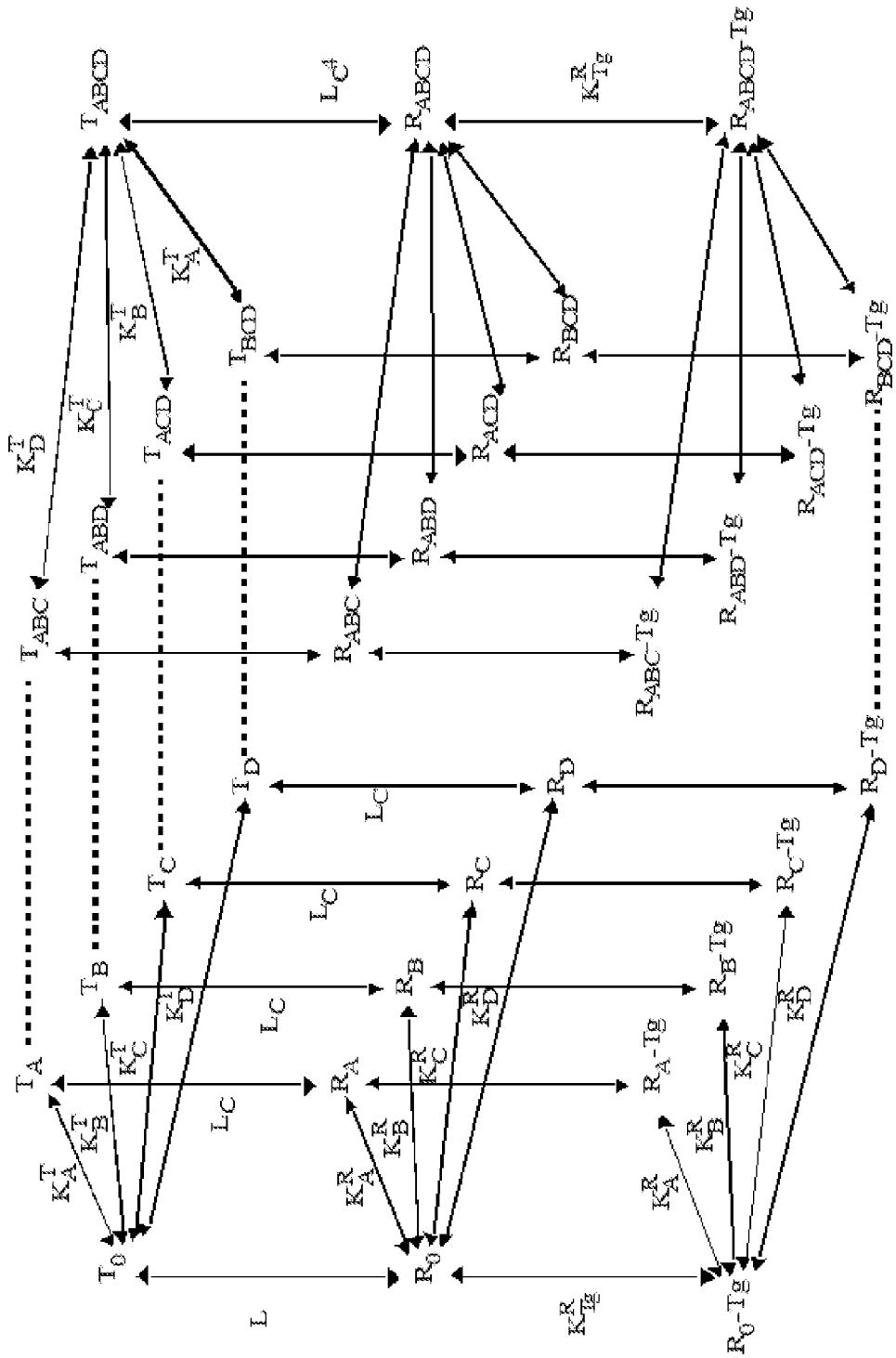
FIG. 8 shows (adapted from [34]) depicts portions of a postulated model for a detailed treatment of calmodulin behavior in a cascade.

Further regarding allosteric enzymes complexity and calmodulin in particular, FIG. 8 (adapted from [34]) depicts portions of a postulated model for a detailed treatment of calmodulin behavior in a cascade. This model turns out to very accurately match empirical measurements that had otherwise been unexplained and also directly matches what would be expected from the ternary enzyme protein folding structure of the calmodulin molecule. This example demonstrates the radically increasing complexity-handling required, and it is noted that this is just one element in a cascade (which in turn is often multiply-branched and surrounded by various feedback loops)—all further motivating the need for an appropriately capable computer tool. The example also demonstrates the value of introducing a model transcendent of specific structural study, something that can be readily provided by a computer tool.

Additionally, this example [34] further demonstrates how quickly aspects that were entirely unknown (here regarding calmodulin, the classic central enzyme of calcium signaling) can emerge and need to become incorporated into many existing models, suggesting the need for a modular interface to accept replacement as well as entirely new models, as is provided for by the present invention. Another motivating example can be found in [29] where after a Ras/RAF/MEK/ERK kinase signaling model without feedback had been long standing, a feedback loop was recently discovered and incorporated in the mathematical model. Additionally, the resulting mathematical model was used to demonstrate detailed behavior of a tumor-suppressing drug. Here again, the need for an ability to amend mathematical models that may be long-standing is demonstrated, as well as the value of these models in drug and therapy discovery [28].

Background on Computer Models of Signaling Pathways

Computer models exist for the numerical simulation of the dynamics of classical enzyme reactions. Most of these are directed to the kinetics of isolated enzyme reactions, although a few are directed towards enzyme cascades in particular. Although useful, in general these computer models do not provide accurate nonlinear structural stability analysis of the larger nonlinear enzyme cascade dynamics (as may be valuable for revealing essential aspects of instability, trajectory bifurcations, sensitivity to outside disturbances at specific points in the signal chain, and other key aspects relating to questions of robustness and failure modes).

The most natural way of representing the dynamics of systems where one state variable controls the gain of another state variable in affecting the rate of change of a third state variable is a system of differential equations with "cross products" among the state variables. This has been repeatedly recognized in many papers on mathematical models of the dynamics of enzyme cascades (see [3] as one example).

In general the detailed dynamics of a number of enzyme cascades comprise nonlinear differential equations, most involving such cross-product terms among state variable. Few researchers can work well with these, or nonlinear differential equations in general, so usually (as in [3, 4], and countless others) these nonlinear differential equations are linearized (removing their nonlinear character) and/or studied in steady-state equilibrium (setting all time derivatives to zero) therefore missing both the intrinsic nonlinearities and intrinsic dynamics. Feedback considerably complicates the picture [5, 6, 16], as do allosteric enzymes [90, 38, 39-44], multiple pathways [16, 28], and cross-talk [21, 31, 37] mingling among the signaling pathways and cascades. The paper [4] attempts to characterize some stability effects of crosstalk effects using gross properties of graph and matroid structures within the matrix arising from linearization of the signaling cascade differential equations. This course of research is noteworthy and in keeping with the notion of "hidden" structural stability implications [23, 33], but suffers from the linearization step throwing out all multiplicative structure among state variables.

There are a number of available computer software modeling tools for modeling or simulating aspects of signaling pathways. These available software modeling tools simulate presented conditions and/or explore linear-algebraic characteristics such as linear eigenmodes (and in some cases offer linear stability analysis). The linear analysis features of these available computer tools are incapable of identifying the dynamics, stability, sensitivity, and other key properties of bilinear differential equations modeling enzyme/kinase cascades. The simulation computer tools that numerically render nonlinear enzyme/kinase cascade differential equation models more precisely can compute and support analysis of simulation results for specified assumed conditions. These cannot identify structural features relating to stability and sensitivity properties of bilinear systems of differential equations modeling enzyme/kinase cascades. Finally, none of the available computer tools appear to provide much in the way of crosstalk study or in variation of ambient chemical environment properties that could affect pathway operation. The fact that none of these software packages provides essential fundamental bilinear stability and sensitivity, crosstalk, or provide support for the study of allosteric pathways [90, 38, 39-44] and hysteresis [19] underscores the value of the modeling portion the present invention.

A more extensive understanding of signaling pathways is becoming increasingly indispensable. Enzyme recovery dynamics, feedback loops [5, 6, 16], allosteric behaviors, exogenous regulatory controls, and signaling cross-talk transform open-loop cascade dynamics into considerably complex form whose pathological behavior and sensitivities are barely understood [45, 46]. The fact that enzyme cascades can integrate multiple input stimuli, radiate outputs over different substrates, and modulate several pathways at the same time [13] cries out for the need for fundamental mathematical honesty and clarity in the basic modeling of such key elements of signaling pathways as well as a far more comprehensive treatment of their composite behavior.

The invention combines a new generation of computer modeling (new in scope, nonlinear treatment, and analysis tools), a model-refinement environment, and a new method of signaling network biochemical measurement and emulation.

More specifically, the invention combines a new generation of computer-based mathematical modeling (larger networks, accurate nonlinear treatment, crosstalk/allosteric/hysteresis support, advanced structural analysis tools), a model-refinement environment, and microfluidic/nanoliter signaling network biochemical measurement and emulation technologies to create new tools and approach for next-generation biological signaling network research and applications.

The invention further provides for the use of microfluidic/nanoliter biochemical signaling pathway devices as analysis/-synthesis/regulatory "biochemical chips" for implant in humans to control disease or pathologies.

Figure 9:
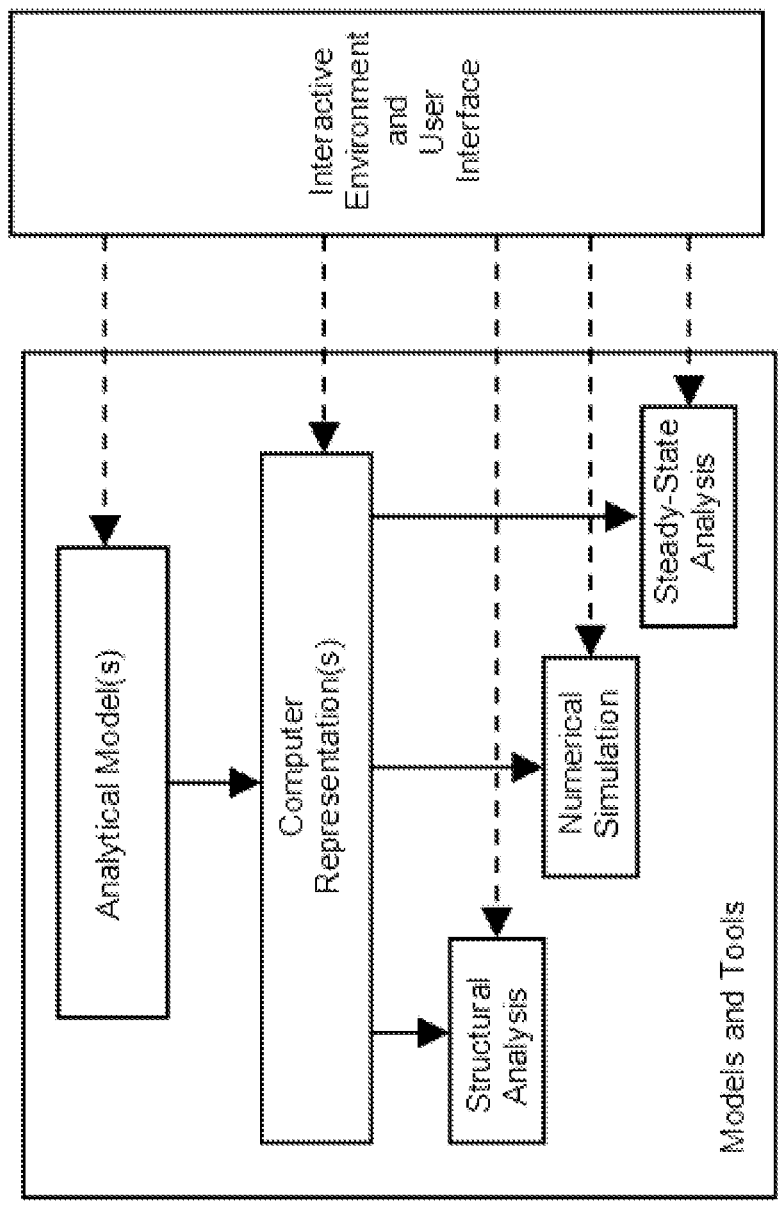
FIG. 9 depicts a basic framework aspect provided for by the invention wherein one or more analytical models of one or more signaling network(s) are represented in a computer for not only steady-state analysis and numerical simulation but also utilizing structural analysis tools designed for sensitivity, non-linear stability, and crosstalk studies.

As to a new generation computer modeling addressing the many bilinear and nonlinear mathematical aspects raised above, FIG. 9 shows an example basic framework provided for by the invention wherein one or more analytical models of one or more signaling network(s) are represented in a computer for not only steady-state analysis and numerical simulation but also focused applicable structural analysis tools designed for sensitivity, non-linear stability, and cross-talk studies. The mathematical modeling system can comprise one or more elements from the computer modeling system taught in the inventor's pending U.S. patent application Ser. No. 12/767,794 "Nonlinear and Lie Algebra Structural Analysis System for Enzyme Cascades, Metabolic Signal Transduction, Signaling Pathways, Catalytic Chemical Reaction Networks, and Immunology."

To date, computer models have hardly been the driver of signaling pathway and signaling network research. Instead, an interactive process such as that of FIG. 10, which depicts a representation traditional manner in which signaling pathway and signaling network research has usually been performed. Such traditional approaches employ a three-way iteration among laboratory measurements (often made with physically large laboratory instruments), analytical reasoning (usually biochemical or biophysical with limited use of computers), and evolving biochemical models. Tremendous accomplishments have been achieved with this paradigm, but more recently new trends have expanded this approach to include mathematical and computer models, as suggested in the representation of FIG. 11. Here, the three-way iteration among laboratory measurements, analytical reasoning, and evolving biochemical models are used to create mathematical models which in turn can be explored on the computer. The allosteric model of calmodulin proposed by [34] (shown in part in FIG. 8) is a good illustrative example of this, wherein the computer model matched measured data so well as to provide a convincing case for allosteric behavior of calmodulin which could be absorbed into analytical reasoning and biochemical models of calmodulin function.

Figure 12A:
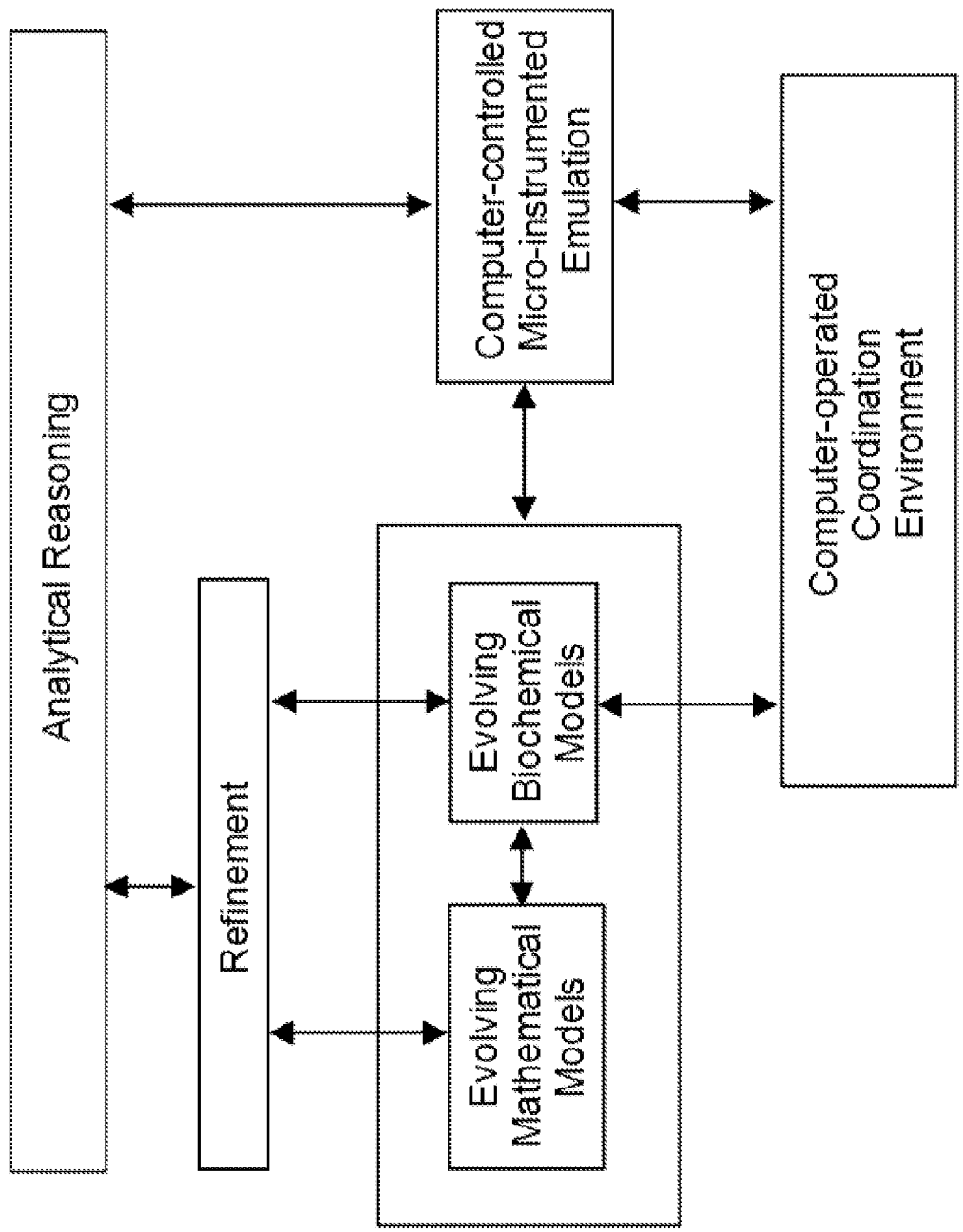
FIG. 12A depicts an example formalized computerized environment as provided for by the invention, providing coupling among a computer-based modeling system, a computer-controlled micro-instrumentation biochemical reaction environment, and a computer-operated coordination environment.
Figure 12B:
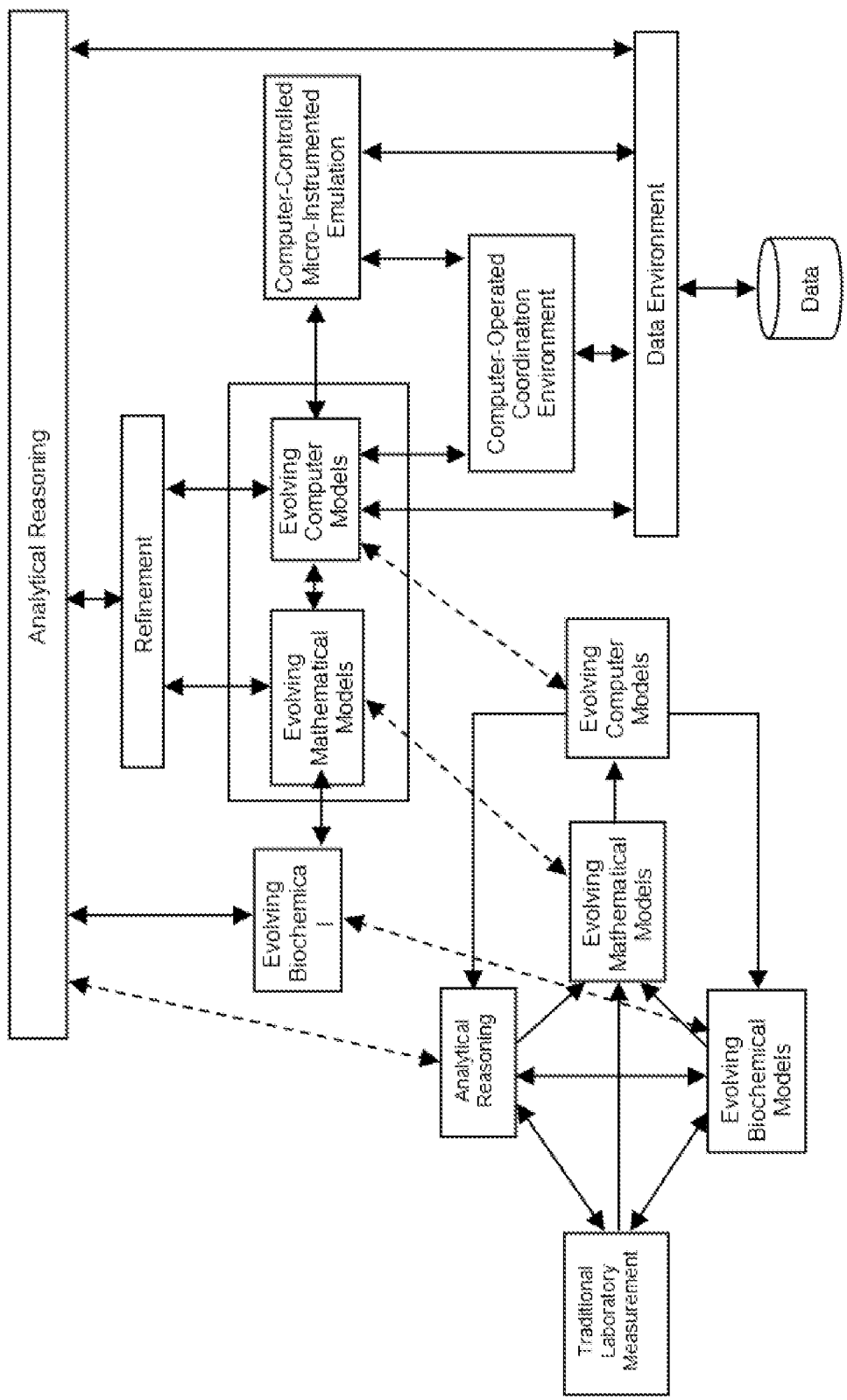
FIG. 12b depicts example interactions among aspects of traditional signaling research approaches, for example as depicted in FIG. 11, and the combined signaling pathway computer modeling and micro-instrumentation tool, for example as the one depicted in FIG. 12A.

Combining Signaling Pathway Computer Models with a Computer-Controlled Micro-Instrumentation Biochemical Reaction System The invention is directed to a more formal computerized environment for work of this type, and providing coupling to a computer-controlled micro-instrumentation biochemical reaction system as shown FIG. 12a and in the upper right portion of FIG. 12b.

More specifically, FIG. 12A depicts an example formalized computerized environment as provided for by the invention, providing coupling among a computer-based modeling system, a computer-controlled micro-instrumentation biochemical reaction system, and a computer-operated coordination environment.

The invention provides for a combined advanced nonlinear computer modeling and computer-controlled micro-instrumented emulation tool includes explicit components for incorporating new discovery, model refinement, a computer operated coordination environment, and (not shown In FIG. 12a) a data management environment.

Figure 10:
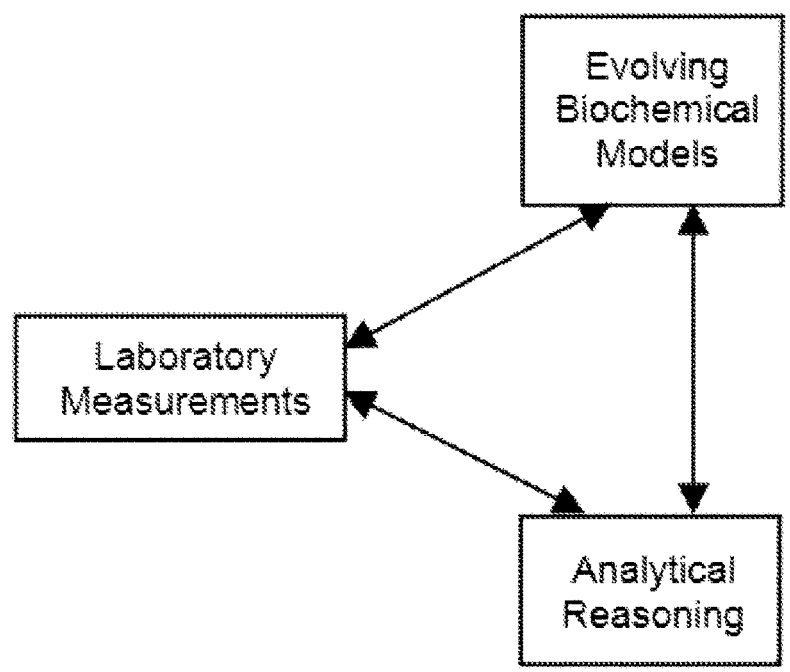
FIG. 10 shows depicts a representation of a traditional manner in which signaling pathway and signaling network research advancement has been performed, namely in three-way iteration among laboratory measurements (often made with physically large laboratory.
Figure 11:
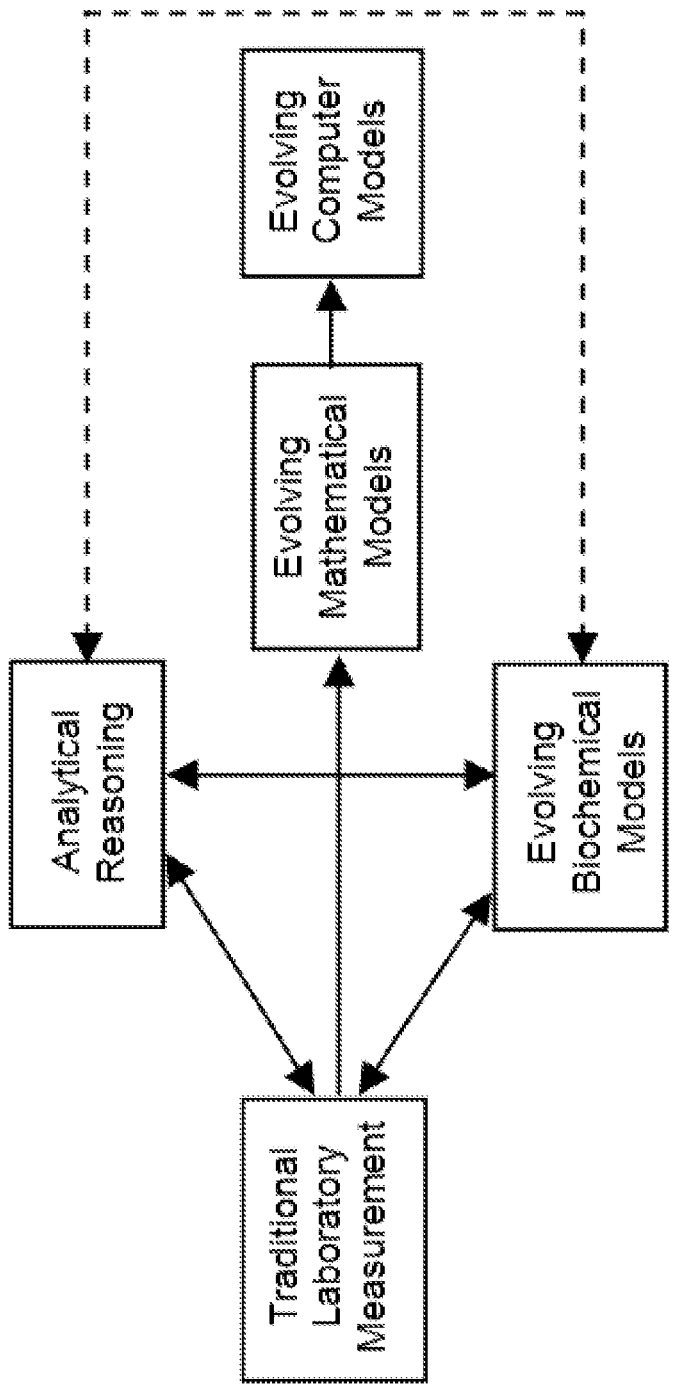
FIG. 11 depicts an example expansion of the traditional signaling research approach represented in FIG. 10 so as to include mathematical and computer models.

Collaborative Applications of the Combined Signaling Pathway Computer Models and Computer-Controlled Micro-Instrumentation Biochemical Reaction System Although the resulting combined signaling pathway computer modeling and micro-instrumentation tool will have important stand-alone value, and additional value magnified by the networking of collaborators using instances of the combined signaling pathway computer modeling and micro-instrumentation tool and exchanging data and models, the tool will also be designed to smoothly interface with traditional signaling research approaches (i.e., those of FIGS. 10-11). FIG. 12b depicts example interactions of this sort among aspects of traditional signaling research approaches, for example as depicted in FIG. 11, and the combined signaling pathway computer modeling and micro-instrumentation tool, for example as the one depicted in FIG. 12A. The resulting exchanges will provide a valuable new method for making important advancements in signaling pathway research, metabolism, disease studies, drug discovery, drug design, and therapy design.

In an implementation, the resulting combined signaling pathway computer modeling and micro-instrumentation tool can be designed with an open architecture and open model format so that data and models may be freely exchanged among researchers, for example using the expanding number of online databases and model repositories [47-56].

Example Applications for the Combined Signaling Pathway Computer Models and Computer-Controlled Micro-Instrumentation Biochemical Reaction System The scope of the envisioned tool can be obviously extensive. An representational example, which is by no means limiting, is directed to the study of signaling pathways involving calmodulin. This example utilizes a rich number of the capabilities of the invention as calmodulin:

Is involved in a large number of signaling pathways and metabolic processes;

Interacts with many types of signaling mechanisms, for example enzyme cascades, metal and chlorine ions, nitric oxide, redox, hormones, etc.;

Is known to be a component in complex signaling comprising feedback, modulation, etc.;

Is subject to crosstalk (for example with Protein Kinase C [21, 31]);

Arguably exhibits (4-level) allosteric behavior [34];

Is involved in pathways implicated in or affected by numerous diseases, illnesses, and pathologies, including cancer [12];

Is deeply involved, along with nitric oxide, in key cell-death (apoptosis) processes;

Permits relatively straightforward micro-instrumentation of concentration level measurements for many associated signal transduction species;

Is well-studied with extensive literature and subject to near-constant new discoveries.

The invention provides for the afore-described system to be used in signaling pathway research.

The invention provides for the afore-described system to be used in drug discovery.

The invention provides for the afore-described system to be used in drug design.

The invention provides for the afore-described system to be used in therapy discovery.

The invention provides for the afore-described system to be used in therapy design.

Computer-Controlled Micro-Instrumentation Biochemical Reaction System

The computer-controlled micro-instrumentation biochemical reaction system can, for example, utilize microfluidic lab-on-a-chip and reconfigurable lab-on-a-chip technologies and technologies to create microfluidic/nanoliter "lab-on-a-chip"—like technologies for micro-scale isolation of reactive intermediates and leveraging these for organic chemical synthesis and analysis.

The invention provides for a computer-controlled micro-instrumentation biochemical reaction system using lab-on-a-chip and reconfigurable lab lab-on-a-chip technology, including but not limited to innovations and material taught in the following pending patent applications:

U.S. Ser. No. 11/946,678, "Reconfigurable Chemical Process Systems."

U.S. Ser. No. 12/328,726, "Software Systems for Development, Control, Programming, Simulation, and Emulation of Fixed and Reconfigurable Lab-on-a-Chip Devices."

U.S. Ser. No. 12/328,716, "Multi-Channel Chemical Transport Bus for Microfluidic and Other Applications."

U.S. Ser. No. 12/328,713, "Software-Controlled Lab-on-a-Chip Emulation."

U.S. Ser. No. 12/931,867 "Chemical Synthesis via Electron Transfer, Excited States, and/or Reactive Intermediates from Integrated and/or Sequential Photochemical and Electrochemical Processes"

The aforementioned micro-instrumentation can include optical detection of markers and other photochemical phenomena. For example, specific types of biochemical markers can be introduced into a confined micro-environment and stimulated with UV light produced by a UV LED that can be detected by a photodetector. For example, UV LEDs with a range of wavelengths as short as 400-240 nm are currently supplied/distributed by Sensor Electronic Technology Inc. (http://www.s-et.com/index.html).

In an embodiment, the photodetector comprises a photodiode. In another embodiment, the photodetector comprises one or more LEDs.

Micro-environment chemistry suitable for microfluidic/lab-on-a-chip implementation is described in pending U.S. patent application Ser. No. 12/931,867.

Associated structures, software, control systems, fluid and gas routing, sensors, electronics, etc is described in these present inventor's pending patent applications:

U.S. Ser. No. 11/946,678, "Reconfigurable Chemical Process Systems."

U.S. Ser. No. 12/328,726, "Software Systems for Development, Control, Programming, Simulation, and Emulation of Fixed and Reconfigurable Lab-on-a-Chip Devices."

U.S. Ser. No. 12/328,716, "Multi-Channel Chemical Transport Bus for Microfluidic and Other Applications."

Figure 13:
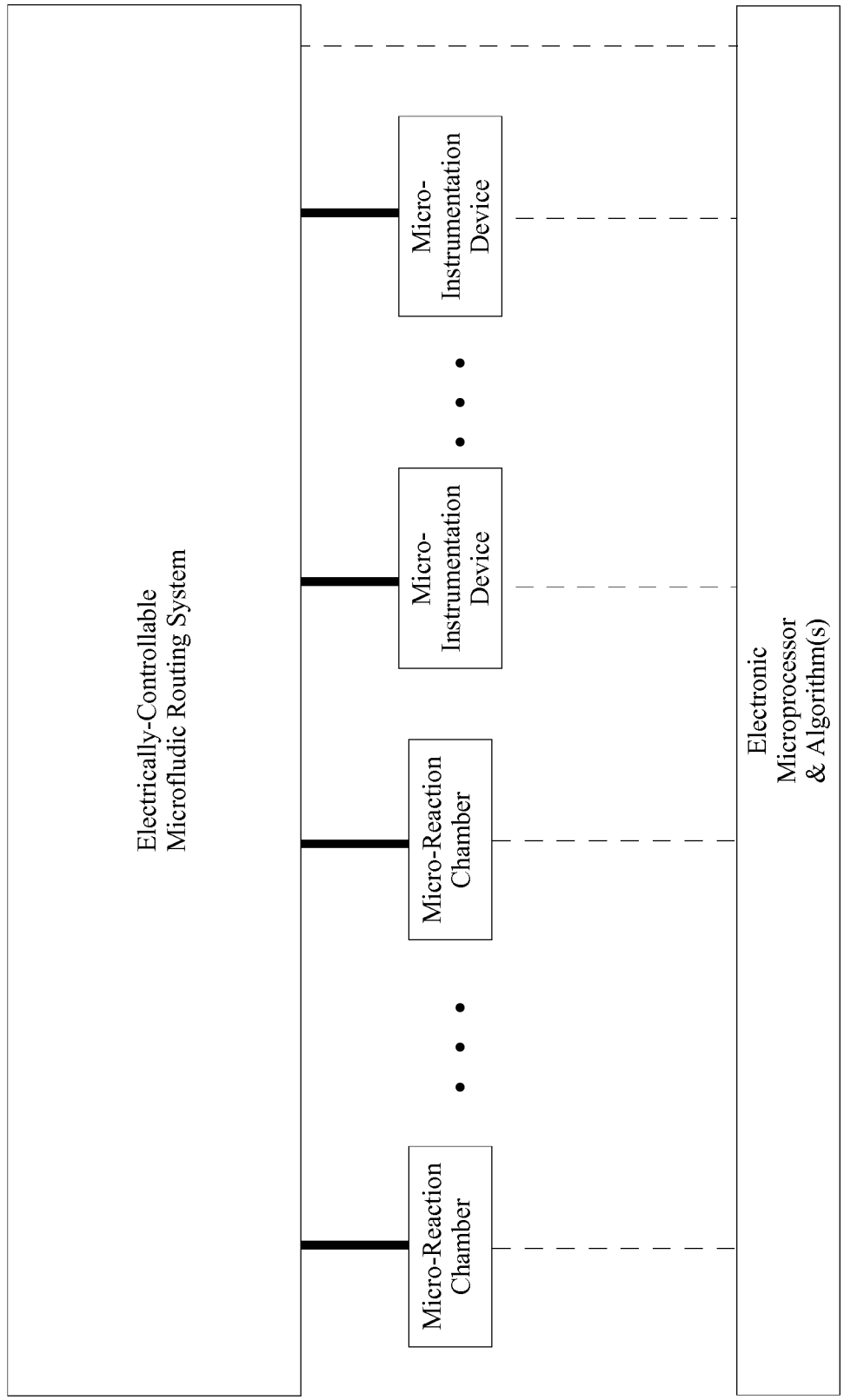
FIG. 13 depicts an example implementation of a microfluidics-based computer-controlled micro-instrumentation biochemical reaction system as provided for by the invention.

FIG. 13 depicts an example implementation of a microfluidics-based computer-controlled micro-instrumentation biochemical reaction system as provided for by the invention.

This example arrangement comprises:

an electrically-controllable microfludic routing system for the controlled transport of picoliter to nanoliter quantities of fluids and gases, the microfludic routing system comprising at least a first electrical interface for receiving electrical signals used for control of the routing of fluids and gases provided by the microfludic routing system;

at least one microreaction chamber for supporting at least one chemical reaction associated with a biological signaling pathway;

at least one micro-instrumentation device for measuring at least one physical quantity associated with the signaling pathway, the micro-instrumentation device producing at least one electrical measurement signal, the micro-instrumentation device further comprising a second electrical interface for transmitting the at least one electrical measurement signal; and at least one electronic microprocessor configured to transmit electrical control signals, to receive electrical measurement signals, and to execute at least one software algorithm;

wherein the microreaction chamber is connected to the microfludic routing system so as to receive at least one of a fluid or gas from the microfludic routing system and to transmit at least one of a fluid or gas to the microfludic routing system; and wherein the electronic microprocessor receives electrical measurement signals from at least the first electrical interface and further transmits electrical control signals to at least the second electrical interface.

Figure 14:
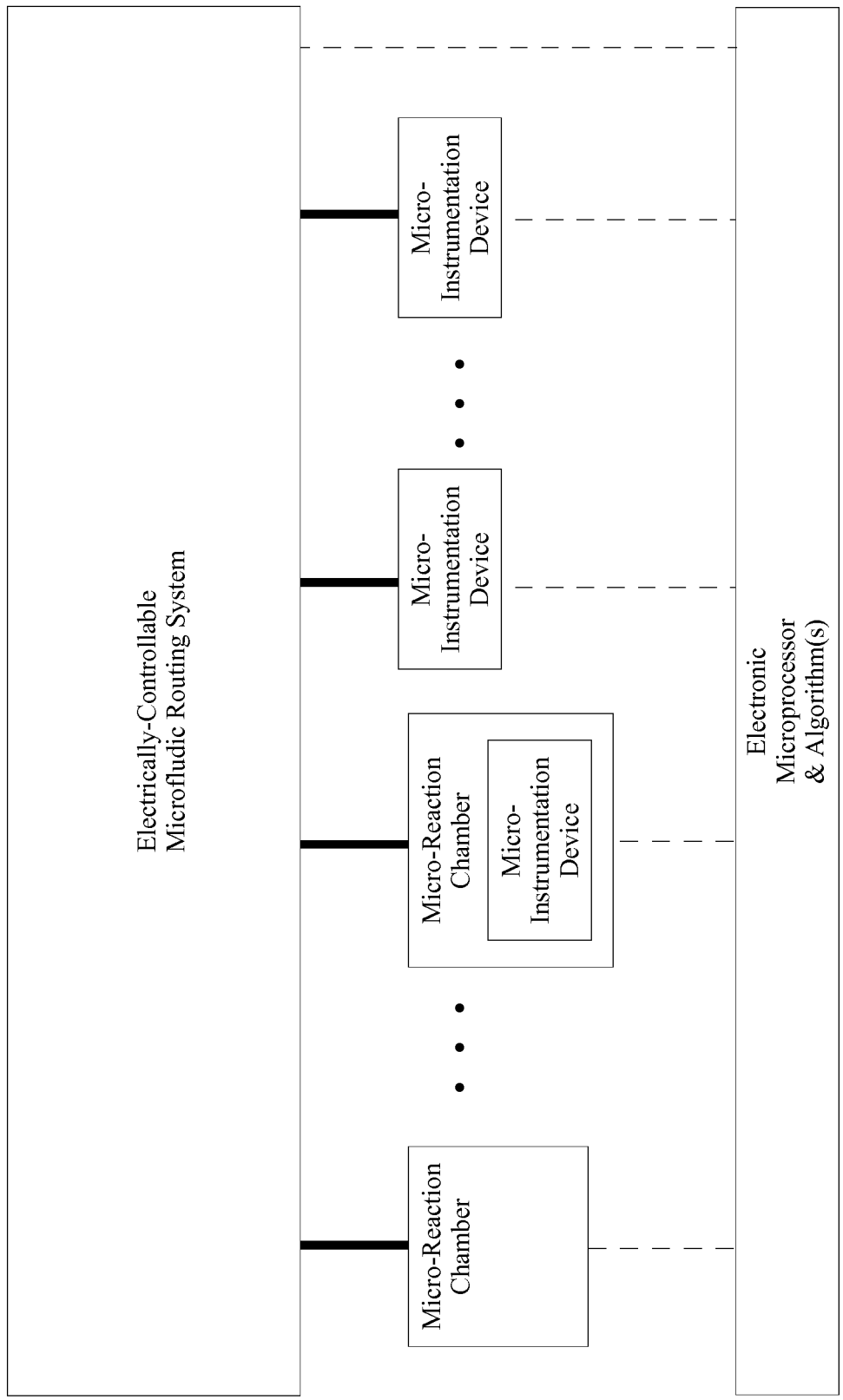
FIG. 14 depicts a variation on the arrangement of FIG. 13 wherein at least one micro-reaction chamber is provided with at least one associated micro-instrumentation device for measurements of materials and/or events inside the micro-reaction chamber.

FIG. 14 depicts a variation on the arrangement of FIG. 13 wherein at least one micro-reaction chamber is provided with at least one associated micro-instrumentation device for measurements of materials and/or events inside the micro-reaction chamber.

Figure 15:
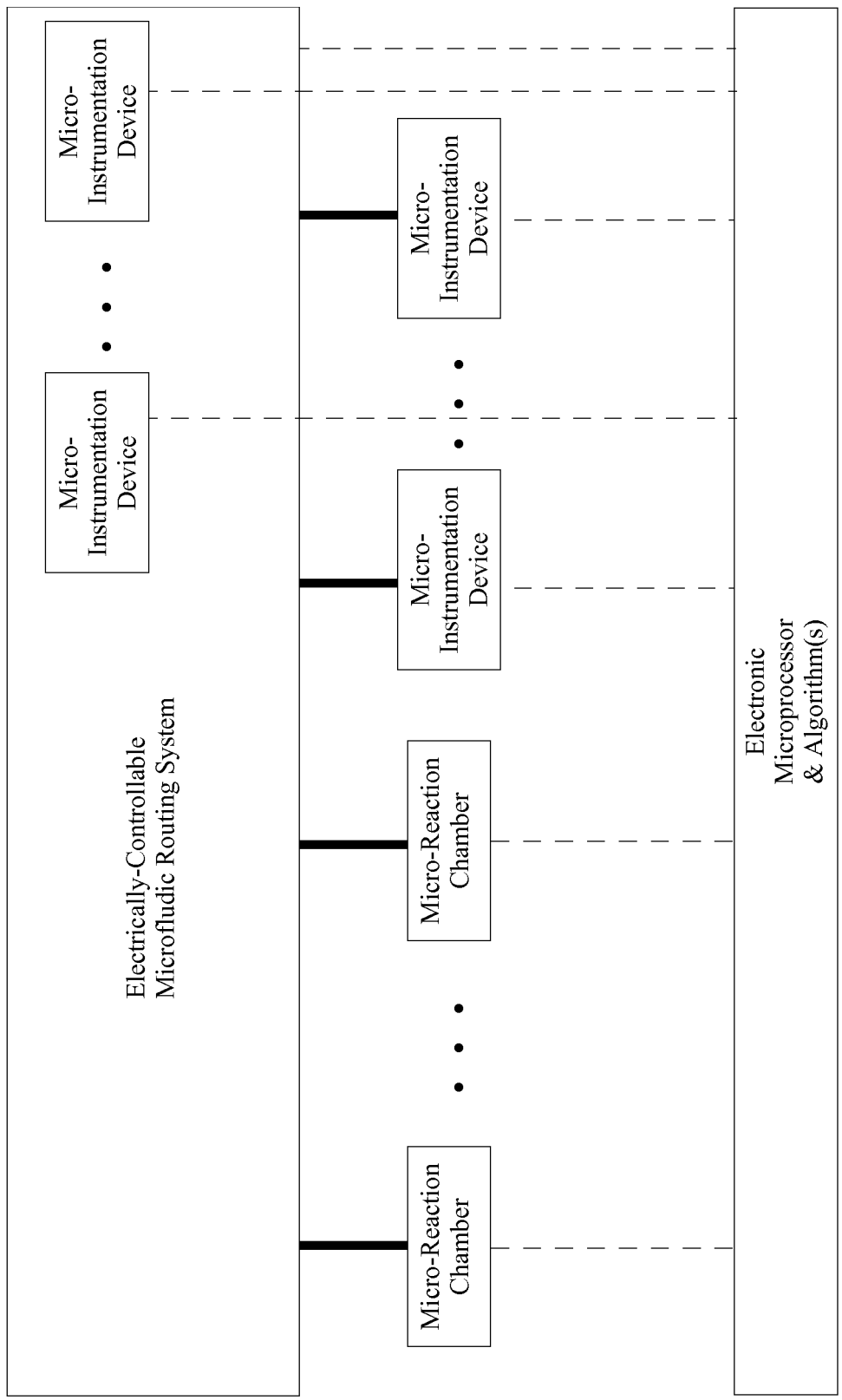
FIG. 15 depicts a variation on the arrangement of FIG. 13 wherein the microfluidic routing system is provided with at least one associated micro-instrumentation device for measurements of materials and/or events inside the microfluidic routing system.

FIG. 15 depicts a variation on the arrangement of FIG. 13 wherein the microfluidic routing system is provided with at least one associated micro-instrumentation device for measurements of materials and/or events inside the microfluidic routing system.

Figure 16:
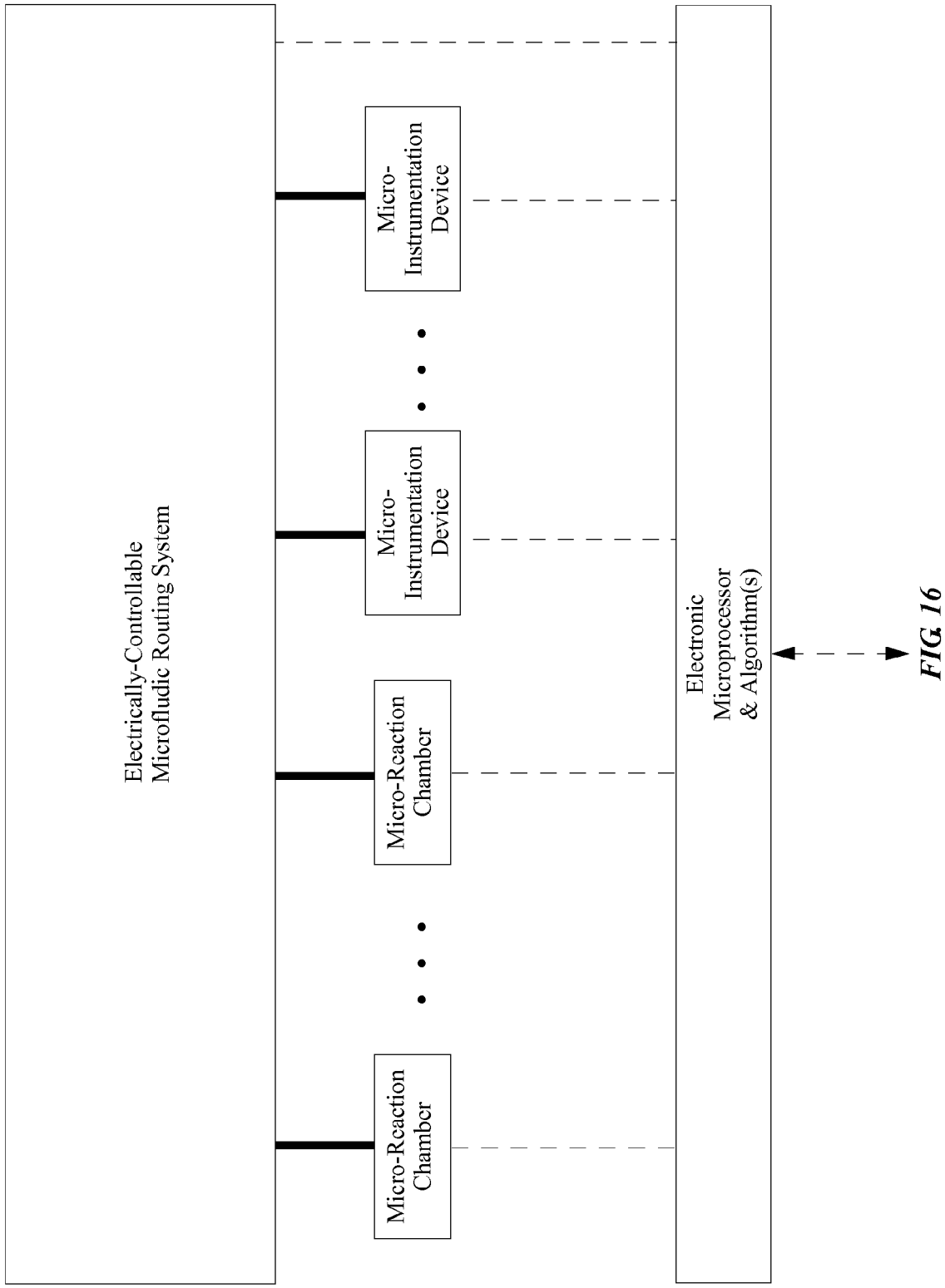
FIG. 16 depicts a variation on the arrangement of FIG. 13 wherein the electrical microprocessor is provided with at least one external signal interface.

FIG. 16 depicts a variation on the arrangement of FIG. 13 wherein the electrical microprocessor is provided with at least one external signal interface.

Figure 17:
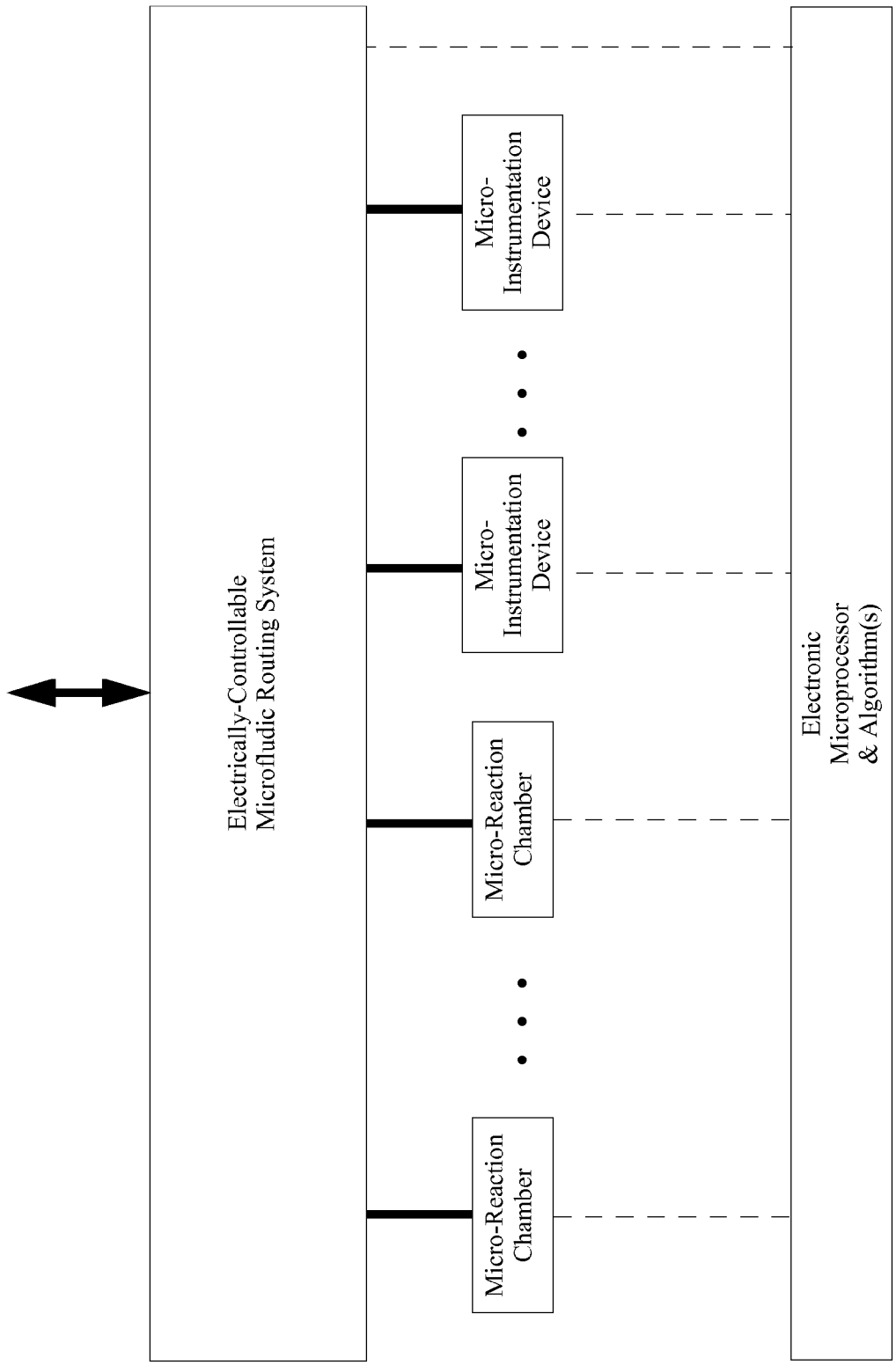
FIG. 17 depicts a variation on the arrangement of FIG. 13 wherein the microfluidic routing system is provided with at least one external interface for the reception and/or transmission of materials such as fluids and/or gases.

FIG. 17 depicts a variation on the arrangement of FIG. 13 wherein the microfluidic routing system is provided with at least one external interface for the reception and/or transmission of materials such as fluids and/or gases.

Figure 18:
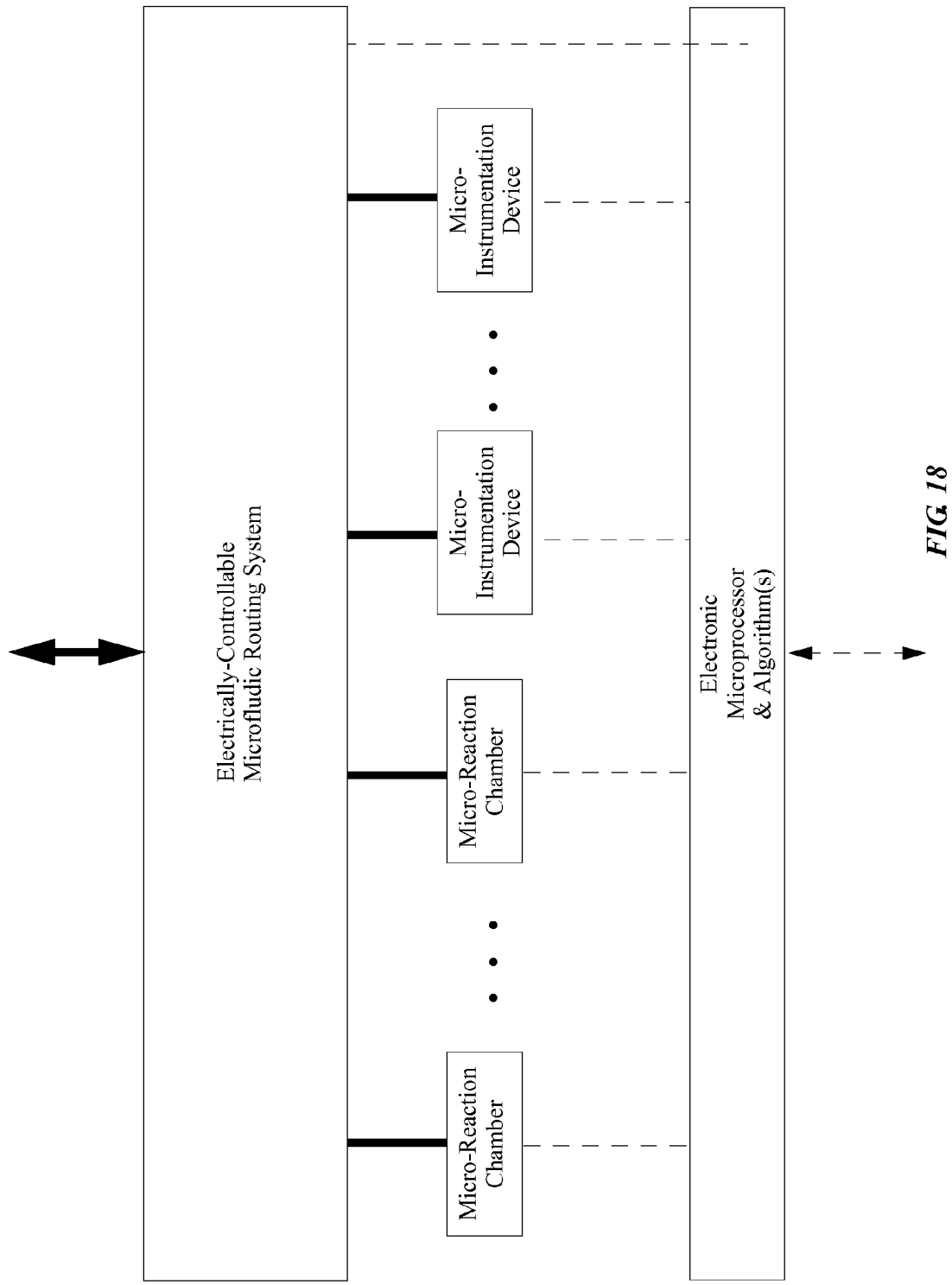
FIG. 18 depicts a variation on the arrangement of FIG. 16 which includes the microfluidic routing system is provided with at least one external interface for the reception and/or transmission of materials such as fluids and/or gases of FIG. 17.

FIG. 18 depicts a variation on the arrangement of FIG. 16 which includes the microfluidic routing system is provided with at least one external interface for the reception and/or transmission of materials such as fluids and/or gases of FIG. 17.

Any of the above arrangements can be used individually or in various combinations.

In another aspect of the invention, the micro-instrumentation device is physically in contact with the contents of the microreaction chamber.

In another aspect of the invention, the micro-instrumentation device is physically in contact with the contents of a fluid or gas travelling through the microfludic routing system.

In another aspect of the invention, the electronic microprocessor is further electrically connected to an external signal interface.

In another aspect of the invention, the electronic microprocessor transmits electrical measurement signals to the external signal interface.

In another aspect of the invention, the electronic microprocessor receives electrical control signals from the external signal interface.

In another aspect of the invention, the algorithm executing on the electronic microprocessor processes information represented in the at least one electrical measurement signal so as to produce a processed measurement data.

In another aspect of the invention, the electronic microprocessor transmits processed measurement data to the external signal interface.

In another aspect of the invention, the algorithm executing on the electronic microprocessor comprises a control algorithm that produces control information used for control of the routing of fluids and gases provided by the microfludic routing system.

In another aspect of the invention, the micro-instrumentation device comprises at least one LED.

In another aspect of the invention, the electronic microprocessor generates LED control signals to control the LED comprised by the micro-instrumentation device.

In another aspect of the invention, the system is further configured for use with numerical signaling pathway model system.

Implantable Biochemical Chip Applications

There are many possible applications for microfluidic/nanoliter "lab-on-a-chip" technology capable of instrumenting and emulating portions of biochemical signaling pathways. Two important example application areas for such technology are:

As considered earlier, use of microfluidic/nanoliter biochemical signaling pathway devices as an emulation component of signaling pathway and drug R&D modeling and emulation systems such as that depicted in FIG. 12a;

Second, use of microfluidic/nanoliter biochemical signaling pathway devices for one or more of monitoring, analysis, synthesis, regulatory, and drug-delivery "biochemical chips" for implant in living organisms (such as humans, animals, or plants) to control and/or monitor disease or pathologies.

Use of the microfluidic/nanoliter biochemical signaling pathway devices provided for by the invention as monitoring, analysis, synthesis, regulatory, drug delivery, and/or therapy delivery "biochemical chips" or other typed of devices for implanting or ingesting in living organisms (such as humans, animals, or plants) so to perform, according to various embodiments, one or more of the following functions:

control of disease processes;
control of pathology processes;
providing of therapies;
monitoring of signaling activity;
monitoring of metabolic activity;
monitoring of gene expression activity;
delivery of drugs;
internal synthesis of drugs;
altering of signaling activity;
altering of metabolic activity;
alerting of gene expression activity.

In another aspect of the invention, the system is further configured for use in living organism as in living organisms for the monitoring of at least one signaling pathway.

In another aspect of the invention, the system is further configured for use in living organism as in living organisms for the monitoring of at least metabolic process.

In another aspect of the invention, the system is further configured for use in living organism for analysis of the operation of at least one signaling pathway.

In another aspect of the invention, the system is further configured for use in living organism as in living organisms for synthesis of a chemical agent for use in affecting at least one signaling pathway.

In another aspect of the invention, the system is further configured for use in living organism as in living organisms for regulation of at least one signaling pathway.

In another aspect of the invention, the system is further configured for use in living organism as in living organisms for regulation of at least one metabolic process.

In another aspect of the invention, the system is further configured for use in living organism to administer a chemical agent for use in affecting at least one signaling pathway.

In another aspect of the invention, the system is further configured for use in living organism to administer a therapy delivery for use in affecting at least one signaling pathway.

The terms "certain embodiments", "an embodiment", "embodiment", "embodiments", "the embodiment", "the embodiments", "one or more embodiments", "some embodiments", and "one embodiment" mean one or more (but not all) embodiments unless expressly specified otherwise. The terms "including", "comprising", "having" and variations thereof mean "including but not limited to", unless expressly specified otherwise. The enumerated listing of items does not imply that any or all of the items are mutually exclusive, unless expressly specified otherwise. The terms "a", "an" and "the" mean "one or more", unless expressly specified otherwise.

While the invention has been described in detail with reference to disclosed embodiments, various modifications within the scope of the invention will be apparent to those of ordinary skill in this technological field. It is to be appreciated that features described with respect to one embodiment typically can be applied to other embodiments.

The invention can be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

Although exemplary embodiments have been provided in detail, various changes, substitutions and alternations could be made thereto without departing from spirit and scope of the disclosed subject matter as defined by the appended claims. Variations described for the embodiments may be realized in any combination desirable for each particular application. Thus particular limitations and embodiment enhancements described herein, which may have particular advantages to a particular application, need not be used for all applications. Also, not all limitations need be implemented in methods, systems, and apparatuses including one or more concepts described with relation to the provided embodiments. Therefore, the invention properly is to be construed with reference to the claims.

REFERENCES

[1] M. Alison and C. Sarraf, *Understanding Cancer—From Basic Science to Clinical Practice*, Cambridge University Press, New York, 1997.

[2] H. T. Banks, R. P. Miech and D. J. Zinberg, "Nonlinear Systems in Models for Enzyme Cascades," from *Variable Structure Systems with Application to Economics and Biology, Lecture Notes in Economics and Mathematical Systems*, vol. 111, pp. 265-277, Springer-Verlag, New York, 1975.

[3] S. Beirer, *Mathematical Modelling of the Jak/Stat1 Signal Transduction Pathway*, Logos Verlag Berlin, 2007.

[4] B. Binder and R. Heinrich, "Dynamic Stability of Signal Transduction Networks Depending on Downstream and Upstream Specificity of Protein Kinases," *Molecular Biology Reports*, pp. 51-55, Kluwer Academic Publishers, 2002.

[5] N. Bluthgen, H. Herzel, "MAP-Kinase-Cascade: Switch, Amplifier, or Feedback Controller?" $2^{nd}$ *Workshop on Computation of Biochemical Pathways and Genetic Networks*, Berlin, Logos-Verlag, 2001, pp. 55-62.

[6] N. Bluthgen, *Dynamical Models of Signal Transduction and the Influence of Feedback Loops*, TU-Berlin Thesis in Physics, June 2002.

[7] Bootman, M.; Berridge, M.; Roderick, H., "Calcium signalling: more messengers, more channels, more complexity," *Current Biology, Vol.* 12, No. 16, pp. R563-5, 2002.

[8] W. M. Boothby, "A Transitivity Problem From Control Theory," from *Journal Differential Equations*, vol. 17, pp. 296-307, 1975.

[9] A. Boyd, *Intracellular Signaling Mechanisms and the Pathophysiology of Disease (Current concepts)*, Boyd, A., Upjohn Company, 1991.

[10] H. Bradlow, L. Castagnetta, L. Massimo, K. Zaenker, *Signal Transduction and Communication in Cancer Cells*, New York Academy of Sciences, 2004.

[11] R. W. Brockett, "On the Reachable Set for Bilinear Systems," from *Variable Structure Systems with Application to Economics and Biology*, A. Ruberti and R. Mohler (Eds.), pp. 54-63, Springer Verlag, Berlin, 1975.

[12] E. Carafoli, M. Brini, *Calcium Signalling and Disease: Molecular Pathology of Calcium (Subcellular Biochemistry)*, Springer, 2007.

[13] María Luz Cárdenas, "Coordination and Homeostasis in the Response to Multiple Signals: Role of Metabolic Cascades," in *Technological and Medical Implications of Metabolic Control Analysis*, ed. Athel Cornish-Bowden and María Luz Cárdenas, Kluwer, pp. 289-298, 2000.

[14] Feinstein, M., "Platelets, Macrophages, and Neutrophils," in R. Mitchell, A. Drummond, C. Downes eds., *Inositol Lipids and Cell Signalling*, Academic Press, London, 1989, pp. 247-281.

[15] D. A. Frank, *Signal Transduction in Cancer*, Kluwer, 2003.

[16] Kholodenko, B., "Untangling the signalling wires," *Nature Cell Biology*, Vol. 9, pp. 247-249, 2007.

[17] R. Kincaid, "Calmodulin-Dependent Protein Phosphatases from Microorganisms to Man," in *The Biology and Medicine of Signal Transduction (Advances in Second Messenger and Phosphoprotein Research)* (Vol 27), S. Shenolikar, A. Nairn ed., Raven Press, 1993.

[18] J. Kucera, "Solution in Large of Control Problem: x=(A u+B v) x," from *Chech. Math. Journal*, vol. 17, pp. 91-96, 1967.

[19] B. Kurganov, "Monocascade Enzyme Systems. Theoretical Analysis of Hysteretic Properties of the Enzyme Initiating the Cascade," from *Biochemistry*, vol. 60, no. 7, pp. 843-849, 1995.

[20] L. F. Ludwig, *Bilinear Controllability Applied to a Geometric Variant of the Holding Problem*, M.S.E.E. thesis, Cornell University, Ithaca, 1980.

[21] M. MacNicol, H. Schulman, "Crosstalk between Protein Kinase C and Multifunctional $Ca^{2+}$/Calmodulin-de-

[22] M. D. Mesarovic and Y. Takahara, *General Systems Theory: Mathematical Foundations*, Academic Press, New York, 1975.

[23] K. Murota, *Systems Analysis by Graphs and Matroids—Structural Solvability and Controllability*, Springer-Verlag, New York, 1987.

[24] R. R. Mohler, *Bilinear Control Processes (Mathematics in Science and Engineering v. 106)*, Academic Press, New York, 1973.

[25] K. Musunuru and P. Hinds, *Cell Cycle Regulators in Cancer*, Karger Landes Systems, New York, 1997.

[26] N. H. Pavel, *Differential Equations—Flow Invariance and Applications*, Pitman, pp. 76-77, 1984.

[27] A. Potapov, "Signal Transduction and Gene Regulation Networks" in B. Junker, F. Schreiber, ed. *Analysis of Biological Networks*, John Wiley & Sons, Inc., Hoboken, 2008.

[28] Rajasethupathy, P.; Vayttaden, S.; Bhalla, U., "Systems modeling: a pathway to drug discovery," Current Opinion in Chemical Biology, Vol. 9, No. 4, pp. 400-406, 2005.

[29] A. Robubi, *RAF Kinases: Pathway, Modulation and Modeling: New—Potentially Irreversible—Kinase Inhibitors, Computational Modeling of the Signaling Cascade, and the Effect of DiRas3 on RAF Signaling*, VDM Verlag Dr. Muller, 2008.

[30] Roderick, H.; Cook, S., "Ca2+ signalling checkpoints in cancer: remodelling Ca2+ for cancer cell proliferation and survival," *Nature Reviews Cancer*, Vol. 8, No. 5, pp. 361-75, 2008.

[31] A. Schmitz, *Investigations of Molecular Interactions of MARCKS-Related Protein: Cross-talk between Calmodulin and Protein Kinase C*, Department of Biochemistry, University of Basil, 1998.

[32] H. Schulman, "The Multifunctional Ca2+/Calmodulin-Dependent Protein Kinase," in *Advances in Second Messenger and Phosphoprotein Research*, Vol. 22, P. Greengard, G. Robison (ed.), Raven Press, 1988.

[33] J. Stelling, S. Klamt, K. Bettenbrock, S. Schuster, E. Gilles, "Metabolic network structure determines key aspects of functionality and regulation," *Nature* 420: pp. 190-193.

[34] M. Stefan, S. Edelstein, N. Le Novere, "An Allosteric Model of Calmodulin explains Differential Activation of PP2B and CaMKII," *PNAS*, vol. 105, No. 31, Aug. 5, 2008, pp. 10768-10773.

[35] T. Traut, *Regulatory Allosteric Enzymes*, Springer, 2007.

[36] J. C. Venter, et al., "The Sequence of the Human Genome," *Science*, vol. 291, Feb. 16, 2001, pp. 1304-51.

[37] Boris Zhivotovsky, Sten Orrenius, "Cell death mechanisms: Cross-talk and role in disease," *Experimental Cell Research*, 316 (2010) 1374-1383.

[38] Klipp, Edda and Wolfram Liebermeister, "Mathematical modeling of intracellular signaling pathways," *BMC Neuroscience*, No. 7 (Suppl. 1):S10, pp. 1-16, 2006.

[39] Najdi, Tarek S., Chin-Rang Yang, Bruce E. Shapiro, G. Wesley Hatfield and Eric D. Mjolsness, "Application of a Generalized MWC Model for the Mathematical Simulation of Metabolic Pathways Regulated by Allosteric Enzymes," *Journal of Bioinformatics and Computational Biology*, v. 4, No. 2, pp. 335-355, 2006.

[40] Lim, Wendell A., "The modular logic of signaling proteins: building allosteric switches from simple binding domains," *Current Opinion in Structural Biology*, v. 12, pp. 61-68, 2002.

[41] del Sol, Antonio, Chung-Jung Tsai, Buyong Ma and Ruth Nussinov, "The Origin of Allosteric Functional Modulation: Multiple Pre-existing Pathways," *Structure Review*, v. 17, pp. 1042-1050, 2009.

[42] Changeux, Jean-Pierre and Stuart J. Edelstein, "Allosteric Mechanisms of Signal Transduction" from *Science*, v. 308, pp. 1424, 2005.

[43] Penchovsky, Robert and Ronald R. Breaker, "Computational design and experimental validation of oligonucleotide-sensing allosteric ribozymes," *Nature Biotechnology*, v. 23, No. 11, pp. 1424-1432, 2005.

[44] Fastrez, Jacques. "Engineering Allosteric Regulation into Biological Catalysts," *Chem Bio Chem*, No. 10, pp. 2824-2835, 2009.

[45] Levine, Arnold J., Wenwei Hu, Zhaohui Feng and German Gilb, "Reconstructing Signal Transduction Pathways: Challenges and Opportunities," *Annals of the New York Academy of Sciences*, v. 1115, pp. 32-50, 2007.

[46] Schwartz, M.; Baron, V., "Interactions between mitogenic stimuli, or, a thousand and one connections," *Curr Opin Cell Biol.*, 11(2):197-202, April 1999.

[47] Campagne, F.; Neves, S.; Chang, C.; Skrabanek, L.; Ram, P.; Iyengar, R.; Weinstein, H., "Quantitative information management for the biochemical computation of cellular networks," *Sci. STKE (The Signal Transduction Knowledge Environment)*, Vol. 2004, Issue 248, 2004.

[48] Hucka M., A. Finney, H. M. Sauro, H. Bolouri, J. C. Doyle, H. Kitano, A. P. Arkin, B. J. Bornstein, D. Bray, A. Cornish-Bowden, et al., "The systems biology markup language (SBML): a medium for representation and exchange of biochemical network models," *Bioinformatics*, v. 19, No. 4, pp. 524-531, 2003.

[49] Olivier, B. G. and J. L. Snoep, "Web-based kinetic modelling using JWS Online," *Bioinformatics*, v. 20, No. 13, pp. 2143-2144, 2004.

[50] Krull, M., N. Voss, C. Choi, et al., "Transpath: an integrated database on signal transduction and a tool for array analysis," *Nucl Acids Res*, v. 31, No. 1, pp. 97-100, 2003.

[51] Lemer C., A. Naim, Y. Zhang, et al., "Amaze: A database of molecular function, interactions and biochemical processes," *In proceedings of molecular informatics on confronting complexity*, May 13th-May 16th, Bozen, Italy, 2002.

[52] Kanehisa, M. and S. Goto, "KEGG: Kyoto Encyclopedia of Genes and Genomes," *Nucl Acids Res*, v. 28, No. 1, pp. 27-30, 2000.

[53] Schomburg, I., A. Chang, O. Hofmann, et al., "BRENDA: a resource for enzyme data and metabolic information," *TRENDS Biochem Sci*, v. 27, No. 1, pp. 54-56, 2002.

[54] Ji, Z. L., X. Chen, C. J. Zhen, et al., "KDBI: Kinetic Data of Biomolecular Interactions database," *Nucl Acids Res*, v. 31, No. 1, pp. 255-257, 2003.

[55] Sivakumaran, S., S. Hariharaputran, J. Mishra, et al., "US The database of quantitative cellular signaling: management and analysis of chemical kinetic model of signaling networks," *Bioinformatics*, v. 19, No. 3, pp. 408-415, 2003.

[56] Nielsen, P., P. Hunter, D. Bullivant, et al., "Cell ML," *Model Respository*. 2004.

I claim:

1. A computer-controlled micro-instrumentation biochemical reaction environment system, the system comprising:
- at least one microreaction device comprising a microreaction chamber for supporting at least one chemical reaction associated with a biological signaling pathway;
- an electrically-controllable microfluidic routing system for the controlled transport of picoliter to nanoliter quantities of fluids and gases, wherein the microfluidic routing system comprises at least a first electrical interface for receiving electrical signals, wherein the microfluidic routing system can transport at least one of a fluid or gas to and/or from the at least one microreaction chamber;
- one or more micro-instrumentation devices associated with a second electrical interface, wherein the one or more micro-instrumentation devices measure a plurality of physical quantities associated with a plurality of aspects of the biological signaling pathway; and
- at least one electronic processor configured to:
  - receive, from at least the second interface, one or more electrical measurement signals associated with the micro-instrumentation device;
- produce processed measurement data based on information in the at least one electrical measurement signal;
- execute at least one numerical simulation modeling aspect associated with the biological signaling pathway;
- determine a control signal to cause at least one chemical reaction associated with a biological signaling pathway based on the numerical simulation modeling; and
- transmit, to the first interface, the control signal to control the routing of fluids and gases provided by the microfluidic routing system.

2. The system of claim 1 wherein the micro-instrumentation device is physically in contact with the at least one fluid or gas in the microreaction chamber.

3. The system of claim 1 wherein the micro-instrumentation device is physically in contact with the contents of a fluid or gas travelling through the microfluidic routing system.

4. The system of claim 1 wherein the electronic processor is further electrically connected to an external signal interface.

5. The system of claim 4 wherein the electronic processor transmits electrical measurement signals to the external signal interface.

6. The system of claim 4 wherein the electronic processor receives electrical control signals from the external signal interface.

7. The system of claim 1 wherein the algorithm executing on the electronic processor processes information represented in the at least one electrical measurement signal so as to produce a processed measurement data.

8. The system of claim 7 wherein the electronic processor transmits processed measurement data to the external signal interface.

9. The system of claim 1 wherein the algorithm executing on the electronic microprocessor comprises a control algorithm that produces control information used for control of the routing of fluids and gases provided by the microfluidic routing system.

10. The system of claim 1 wherein the micro-instrumentation device comprises at least one LED used to provide a source of light utilized in the operation of the micro-instrumentation device.

11. The system of claim 10 wherein the electronic processor generates control signals to control the LEDs.

12. The system of claim 1 wherein the first electrical interface and the second electrical interface are comprised within a common communications arrangement.

13. The system of claim 1 wherein the system is further configured for use in living organisms for the monitoring of at least one signaling pathway.

14. The system of claim 1 wherein the system is further configured for use in living organisms for the monitoring of at least one metabolic process.

15. The system of claim 1 wherein the system is further configured for use in living organisms for analysis of the operation of at least one signaling pathway.

16. The system of claim 1 wherein the system is further configured for use in living organisms for synthesis of a chemical agent for use in affecting at least one signaling pathway.

17. The system of claim 1 wherein the system is further configured for use in living organisms for regulation of at least one signaling pathway.

18. The system of claim 1 wherein the system is further configured for use in living organisms for regulation of at least one metabolic process.

19. The system of claim 1 wherein the system is further configured for use in living organisms to administer a chemical agent for use in affecting at least one signaling pathway.

20. The system of claim 1 wherein the system is further configured for use in living organisms to administer a therapy delivery for use in affecting at least one signaling pathway.

* * * * *